United States Patent [19]
Law et al.

[11] Patent Number: 5,656,426
[45] Date of Patent: Aug. 12, 1997

[54] FUNCTIONAIZED HYDROPHILIC ACRIDINIUM ESTERS

[75] Inventors: Say-Jong Law, Westwood, Mass.; Chariklia Sotiriou-Leventis, Rolla, Mo.; Anand Natrajan, Manchester, N.H.; Qingping Jiang, Northborough, Mass.; Peter B. Connolly, Walpole, Mass.; John P. Kilroy, Boston, Mass.; Constance R. McCudden, Brookline, Mass.; Stephen M. Tirrell, Franklin, Mass.

[73] Assignee: Chiron Diagnostics Corporation, Medfield, Mass.

[21] Appl. No.: 225,165

[22] Filed: Apr. 8, 1994

Related U.S. Application Data

[60] Continuation-in-part of Ser. No. 32,231, Mar. 17, 1993, Pat. No. 5,449,556, which is a division of Ser. No. 826,186, Jan. 22, 1992, Pat. No. 5,227,489, which is a continuation of Ser. No. 226,639, Aug. 1, 1988, abandoned.

[51] Int. Cl.$^6$ ...................................................... C12Q 1/68
[52] U.S. Cl. ........................... 435/6; 546/108; 436/543; 436/172; 252/301.21; 552/638
[58] Field of Search ........................ 546/108, 102, 546/105, 110; 435/6; 436/543, 172; 252/201.21; 552/638

[56] References Cited

U.S. PATENT DOCUMENTS

| 4,031,117 | 6/1977 | Rao | 260/397 |
|---|---|---|---|
| 4,197,286 | 4/1980 | Rao | 424/1 |
| 4,745,181 | 5/1988 | Law et al. | 530/387 |
| 5,241,070 | 8/1993 | Law | 546/107 |
| 5,281,712 | 1/1994 | McCapra et al. | 546/104 |
| 5,283,334 | 2/1994 | McCapra | 546/104 |
| 5,284,951 | 2/1994 | McCapra et al. | 546/107 |
| 5,284,952 | 2/1994 | Ramakrishnan | 546/104 |
| 5,290,936 | 3/1994 | Beheshti et al. | 546/104 |
| 5,321,136 | 6/1994 | McCapra | 546/104 |

FOREIGN PATENT DOCUMENTS

| A 0082 636 | 6/1983 | European Pat. Off. | C07D 401/12 |
|---|---|---|---|
| 0273115 | 7/1988 | European Pat. Off. | C07D 219/16 |
| A 0322 926 | 12/1988 | European Pat. Off. | G01N 33/53 |
| A 0353 971 | 2/1990 | European Pat. Off. | C07D 219/04 |
| 2232995 | 7/1989 | United Kingdom | C07D 211/82 |

OTHER PUBLICATIONS

Hammond et al., J. Bioluminescence and Chemiluminescence 6:35–43 (1991).
Weeks et al., Clin. Chem. 29(8):1474–1479 (1983).
Matthews et al., Analytical Biochemistry 169, 1–25 (1988).
Bonfanti, C. et al., 1985a, J. Virolog. Meth. 11: 161–170.
Bonfanti, C. et al., 1985b, J. Clin. Microbio. 21(6): 963–968.
Crosby, S.R. et al., 1986, J. Steroid Biochem. 25: 957–962.
Forsgren, M., 1985, Reviews of Infec. Diseases 7(Supp.1): S129–S132.
Isaac and Payne, 1982, J. Med. Virology 10: 55–64.
Law, S.–J. et al., 1989, J. Biolum. and Chemilum. 4: 88–98.
Rao and Moore, Jr. 1976, Steroids 28: 101–109.
Rao and Taraporewala, 1993, Steroids 57: 154–161.
Ruegg et al, 1974, 6 Int. J. Peptide Protein Res. 447–456.
Seppanen, H., 1990, J. Clin. Microbio. 28(4): 719–723.
Steece, R. S. et al., 1984, J. Clin. Microbio. 19(6): 923–925.
White, A. et al., 1985, J. Steroid Biochem. 23: 981–989.
Wielaard, F. et al., 1985, J. Virolog. Meth. 10: 349–354.

Primary Examiner—Scott W. Houtteman
Attorney, Agent, or Firm—Arthur S. Morgenstern; Robert Blackburn

[57] ABSTRACT

Novel acridinium esters that are useful, either alone or when incorporated into liposomes, as chemiluminescent agents in binding assays (e.g., immunoassays and gene probe assays) with improved-sensitivity are disclosed. In addition, the synthesis of these esters and their use in assays for detecting an analyte is described. In particular, assays for testosterone and the Rubella virus are disclosed.

31 Claims, 9 Drawing Sheets

DMAeE-NHS    DMAE-NHS

FUNCTIONAIZED HYDROPHILIC ACRIDINIUM ESTERS

This is a continuation-in-part of application Ser. No. 08/032,231 filed on Mar. 17, 1993, and issued as U.S. Pat. No. 5,449,556 which is a divisional application of Ser. No. 07/826,186 filed on Jan. 22, 1992, and issued as U.S. Pat. No. 5,227,489, which was a continuation of application Ser. No. 07/226,639 filed on Aug. 1, 1988, now abandoned.

FIELD OF THE INVENTION

The present invention relates to a novel method for detection of an analyte. The present invention relates to the detection of an analyte using acridinium esters as chemiluminescent markers which can be encapsulated within liposome vesicles without significant leakage of the esters from the vesicles. The present invention also relates to the synthesis and use of novel functionalized hydrophilic acridinium esters which are useful as chemiluminescent labels, and suprisingly give a much higher quantum yield than prior acridinium ester compounds. The present invention also relates to novel hydrophilic acridinium esters which may be used to form direct and indirect conjugates. The present invention also relates to novel conjugates formed from such functionalized hydrophilic acridinium ester compounds. The present invention further relates to assays utilizing these novel functionalized hydrophilic acridinium esters and conjugates thereof. The instant invention relates to immunoassay using the compounds of the instant invention.

BACKGROUND OF THE INVENTION

The use of acridinium esters as chemiluminescent labels in clinical assays is known. For example, European Patent Application No. 82 306 557.8 describes the use of an aryl acridinium ester activated with an N-hydroxy-succinimidyl moiety as a chemiluminescent label in immunoassays. U.S. Pat. Nos. 4,745,181; 4,918,192; 5,241,070, and Copending U.S. patent application Ser. Nos. 08/032,947 filed Jan. 26, 1994, and 08/032,085 filed Mar. 17, 1993, describe polysubstituted aryl acridinium esters (PAAE) which are useful in immunoassays and nucleic acid hybridization assays. U.S. Pat. No. 5,227,489 and Copending divisional U.S. patent application Ser. No. 08/032,231 filed Mar. 17, 1993 which is the parent to the instant application, describe hydrophilic polysubstituted aryl acridinium esters and lumisome conjugates thereof useful in clinical assays, particularly those assays involving liposomes.

Previous methods for the synthesis of 2',6'-Dimethyl-4'-(N-succinimidyloxycarbonyl)phenyl-10-Methyl-9-acridinecarboxylate Methylsulfate (DMAE-NHS) as described in U.S. Pat. No. 4,745,181, require the use of a phenoxy group substituted with a benzyloxycarbonyl group as an intermediate to form the acridine ester via a long synthetic pathway. It is desirable to develop new and efficient methods of synthesizing the useful acridinium ester labels of the instant invention. The unexpected ability to form 2'6'-dimethyl-4'-(N-succinimidyloxycarbonyl)phenyl 9-acridinecarboxylate (DMAeE-NHS) by the simplified procedure of combining a solution of succinimidyl 3,5-dimethyl-4-hydroxybenzoate and 4-dimethylaminopyridine with 9-acridinecarbonyl chloride hydrochloride, was not readily predictable in view of the coexistence of two reactive leaving groups in the same reaction, an acid chloride from 9-acridinecarbonyl chloride and a succinimidyl ester from succinimidyl 3,5-dimethyl-4hydroxybenzoate. For example, in the case where N-succinimidyl 3(4-hydroxyphenyl)-propionate is reacted with the 9-acridinecarbonyl chloride referred to above, the condensation can be carried out under mild conditions (approximately room temperature) due to the absence of the two methyl groups in the ortho positions. (See for example U.S. Pat. No. 4,946,958, cols. 4–5, where the reactant does not contain the ortho-substituted methyl groups.) On the other hand, when the two methyl groups are present, much more drastic conditions (100 degrees C. for 2 hours) are required for the condensation reaction to take place, due to the steric hindrance caused by the methyl groups. It should be noted, though, that there is a benefit provided by the presence of the methyl groups, namely the added stability of the resulting acridinium ester, as discussed, for example, in U.S. Pat. No. 4,745,181.

The lipophilic nature of the prior art acridinium esters and other chemiluminescent compounds render them unsuitable for encapsulation within liposomes because of their rapid leakage through the liposome wall. Additionally, the limited water solubility of prior art acridinium esters and other chemiluminescent compounds only allow the encapsulation of a few marker molecules per liposome vesicle, resulting in relatively low signal amplification.

The novel functionalized hydrophilic acridinium esters of the instant invention are useful in immunoassay, yield results that are superior in sensitivity to prior methods, and do not need to use dangerous radiolabels, or organic enzyme/substrates. The use of chemiluminesent labels of this type resulted an unexpected improvement over prior methods and can lead to the functional improvement of previously inoperable or inaccurate assay methodologies. The novel discovery that hydrophilic acridinium esters of the instant invention could be used to label biomolecules and compounds directly without reducing the solubility of the complex allows for many applications in the field of immunoassay. The novel compounds of the instant invention will allow for sensitive immunoassay without the need of excessive use of reagents in the reaction mixture, and are thus designed to reduce non-specific interactions, while not interfering with desired specific interactions.

Another unexpected benefit of having an PAAE carrying a hydrophilic moiety, particularly as a substituent at the nitrogen atom of the acridinium nucleus, is the significant improvement of the chemiluminescent quantum yield relative to that of acridinium esters which simply have an alkyl group (U.S. Pat. No. 4,745,181) or carboxymethyl group (G. Zomer et al., 1989, Anal. Chem. Acta 227: 11–19) substituted at the same position.

The area of immunoassay is well developed, and it is the discovery of unique labeling systems that can spur a quantum advancement in the field of immunoassay. In the field of immunoassay it is desirable to have assays which are highly specific, and highly sensitive to low concentrations, and yet still yield detectable and distinguishable signals for measurement. The instant invention allows for the specific detection of analytes at low concentration, without loss of solubility. The instant invention provides a means for making many specific labeling agents which can be used to detect low levels of analytes. The instant invention also teaches one with ordinary skill in the art, a novel and useful means of performing immunoassay that lends itself readily to automation and commercialization as assay kits and reagent kits.

The application of the novel acridinium esters of the instant invention in conjugates with bioactive proteins such as avidin, antibodies, DNA binding proteins, histones, and ribosomes, and others, is made possible by the hydrophilic properties of the synthesized compounds. These novel acridinium esters are also useful for the labeling of isolated, or intact, RNA, DNA, proteins, peptides, inactivated protein, neurotransmitters, hormones, viruses, viral antigens, bacteria, bacterial antigens, toxins, cytokines, antibody fragments, receptor proteins and other such targets both in vitro, and in vivo. The sampling of tissue samples, serum samples or other such biological samples, and the detection of previously difficult to measure specific analytes in rapid assays, are made possible by the compositions and methods of the instant invention.

One specific application of the instant invention is in the field of pathogen detection. While there have been many assays developed to detect viral pathogens, such as Rubella, the instant invention provides a unique and highly sensitive assay which is unexpectedly superior to previous chemiluminescent methods. The instant methods are comparable with conventional assays in sensitivity yet are more efficient in time required to perform the assay.

Another application of the instant invention is in the area of detection of hormones or haptens or other small biologically active molecules in biological samples. Where the hormone or hapten levels are low, and transient, it is useful to have a sensitive and rapid method of testing for, and measuring the levels of, hormones or haptens in such biological samples. One of the possible examples is the detection of steroid hormone levels such as testosterone. Detection of testosterone using homologous and heterologous hapten conjugates is known. In this methodology, antibodies are generated to one form of testosterone immunogen. Then said antibodies are used to detect testosterone in a sample, while a conjugated competitive hapten tracer, that is of a different form than the immunogen, is added. Homologous assays are burdened with unacceptably high cross-reactivity such as when using C4-testosterone-B-gal conjugate haptens, and T-3-O-CMO-glucoamylase conjugates. Somewhat lower crossreactivity has been obtained with 11a-substituted hapten-HRP, and T-3-O-CMO hapten-penicillinase (Rao et al., 1992, Steroids 57: 154–162). The instant invention provides for superior detection over prior heterologous hapten assay in that the hydrophilic acridinium ester labels of the instant invention contribute to reduced non-specific interactions.

Accordingly, it is the purpose of the instant invention to provide novel functionalized hydrophilic acridinium esters and conjugates thereof for use as chemiluminescent tracers. It is also a purpose of the instant invention to provide for novel methods of detecting an analyte using functionalized hydrophilic acridinium esters and conjugates thereof. It is also a purpose of the instant invention to provide a new improved synthetic procedure for the efficient production of acridine esters.

SUMMARY OF THE INVENTION

Novel acridinium esters that are useful, either alone or when incorporated into liposomes, as chemiluminescent agents in binding assays (e.g., immunoassays and gene probe assays) with improved sensitivity are disclosed. In addition, the synthesis of these esters and their use in assays for detecting an analyte is described. In particular, assays for testosterone and the Rubella virus are disclosed.

DESCRIPTION OF THE INVENTION

Figure 1:
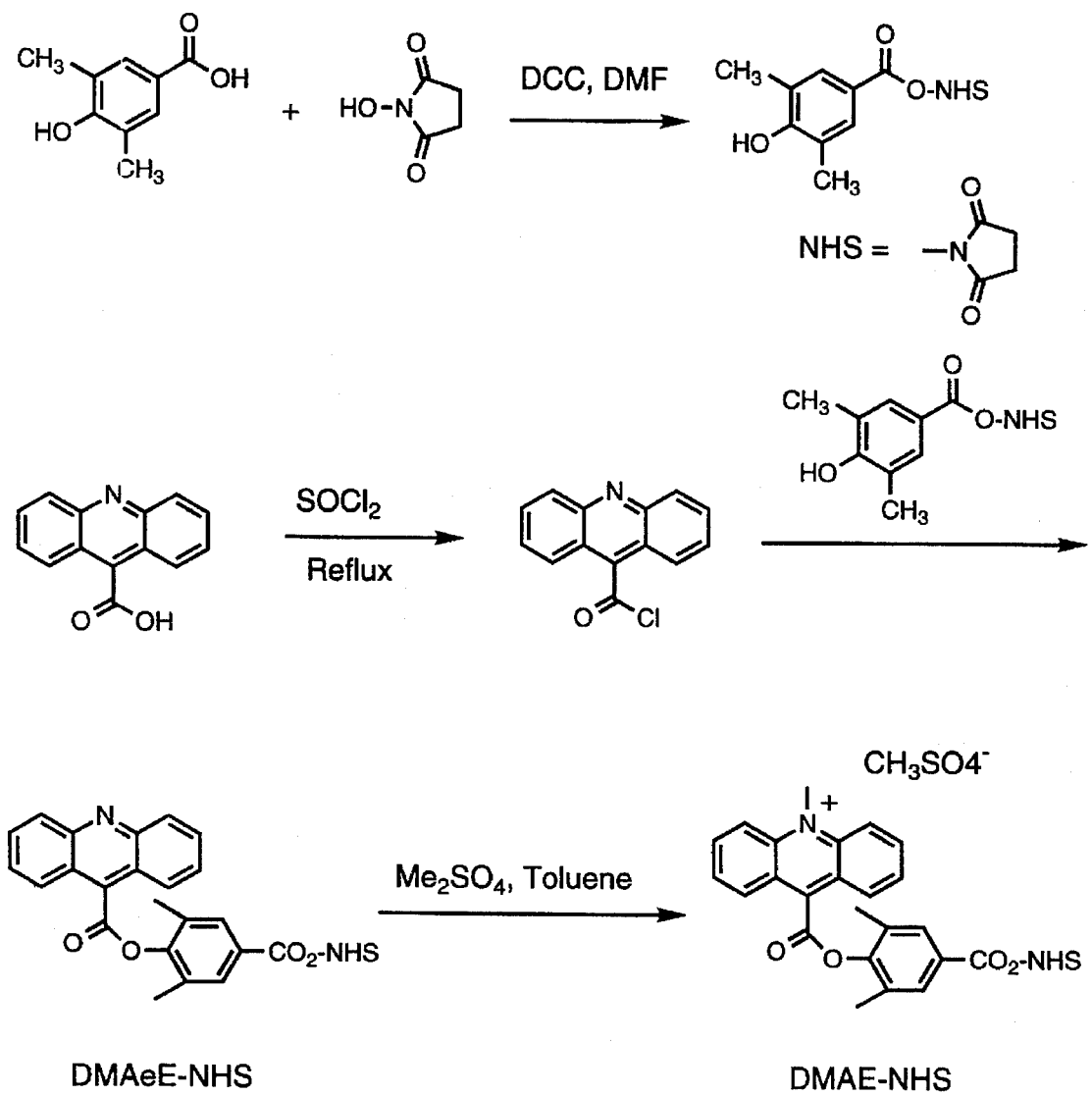
FIG. 1 is a diagram illustrating the improved synthesis of DMAE-NHS.

The following terms as used in the specification and claims shall have the following meanings:

Analyte—the compound or composition to be measured which can be a ligand that is mono- or polyepitopic, antigenic, or haptenic. The analyte can be a piece of DNA or RNA. The analyte can be found in liquid or on solid support.

Conjugates—the combination of chemiluminescent compound with a second compound or molecule. Such conjugates can have many chemiluminescent molecules per second compound.

Indirect Conjugate—the combination of chemiluminescent compound with a second compound or molecule. The combined chemiluminescent compound with a second compound or molecule is then capable of further combining with a third compound or molecule. Such conjugates can have many chemiluminescent molecules per complex.

Homologous—the same compound linked by the same linker, at the same position.

Heterologous—the compound linked by a different linker at a different position, a different linker at the same position, the same linker at a different position.

Linker—a physical or chemical bridge, tie, connection between two compounds or molecules; bifunctional or multifunctional linker. The binding of a linker to one compound can allow for a reactive site to be made availible for further reaction.

Hapten—an incomplete antigen, incapable by itself to provoke an immune response, but when suitably attached to another molecule becomes capable of producing antibodies which will specifically recognize the hapten.

The acridinium esters embodied by the instant invention, and useful in the methods of the instant invention, can be any acridinium ester which is a hydrophilic acridinium ester, a functionalized form of such compound, or conjugate thereof, and which can generate a chemiluminescent signal. The hydrophilic PAAE of the instant invention, with an additional electrophilic or leaving group is useful for conjugation to many targets. The hydrophilic moiety of such a PAAE (comprising an alkyl spacer carrying a highly ionizable group such as sulfonate, phosphonate, sulfate, phosphate) is responsible for enhancing the aqueous solubility, hence reducing the hydrophobic nature of the tracers, particularly those formed from conjugating the PAAE with small organic biomolecules such as steroids, therapeutic drugs, and other controlled chemical substances. When applied in labelling macro-biomolecules such as proteins, nucleic acids, and polysaccharides, the hydrophilic PAAE permits the increase in incorporation ratio (defined as number of PAAE molecules covalently attached to a single macro-biomolecule) without any resulting solubility problems. Thus the increase in specific activity and washability of the tracer would be a factor in enhancing the binding assay sensitivity and improved signal/noise ratio. The lipophilic nature of the prior art acridinium esters and other chemiluminescent compounds render them difficult to use when conjugated to certain biological compounds since there was a significant amount of non-specific binding due to the hydrophobic nature of the tracer conjugate. Thus the prior art acridinium esters and other chemiluminescent compounds were not efficient for use when detection required fine distinction between signal from specific vs. non-specific binding, and resulted in an increased risk of false positive or false negative results.

Preferred functionalized acridinium esters include acridinium esters of the following formula:

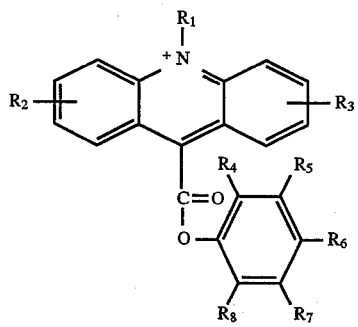

wherein $R_1$ is alkyl, alkenyl, alkynyl, aryl or aralkyl, having up to 24 carbons and up to 20 heteroatoms selected from the group consisting of nitrogen, oxygen, phosphorous and sulfur;

$R_2$, $R_3$, $R_5$, and $R_7$ are hydrogen, amino, hydroxyl, halide, nitro, —CN, —SO$_3$H, —SCN, -R, —OR, —NHCOR, —COR, —COOR, or —CONHR, wherein R is alkyl, alkenyl, alkynyl, aryl, or aralkyl, having up to 24 carbons and up to 20 heteroatoms selected from the group consisting of nitrogen, oxygen, phosphorous, and sulfur;

$R_4$ and $R_8$ are alkyl, alkenyl, alkynyl, aralkyl or alkoxyl having up to 8 carbons, with no branching wherein the side chain groups have more than 2 carbons;

$R_6$ represents the following substitutions: $R_6=R_9-R_{10}$ where $R_9$ is not required but optionally can be an alkyl, or aralkyl group, having up to 5 heteroatoms selected from the group of Phosphorus, Sulfur, Nitrogen, Oxygen, and $R_{10}$ is an electrophile, a leaving group or a group with these two combined natures, as shown in the following examples:

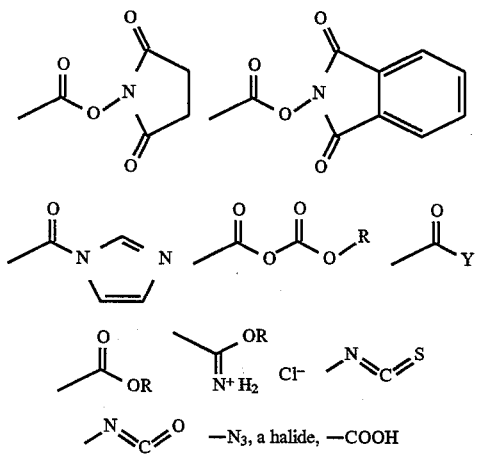

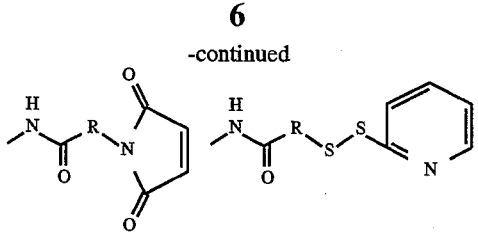

where Y is a halide and R is alkyl, aryl, aralkyl group, and; where $R_5$, $R_6$, and $R_7$ sustituent positions on the phenoxy ring are interchangeable.

Most preferably, R1 is a sulfopropyl or sulfoethyl group; $R_2$ is a hydrogen, methoxy, ethoxy, nitro or halogen; $R_3$, $R_5$, and $R_7$ are hydrogen; $R_4$ and $R_8$ are methyl, ethyl or isopropyl groups; $R_6$ is N-succinimidyloxycarbonyl, N-succinimidyloxycarbonylalkyl, or carboxylate.

It was unexpectedly found that PAAE with the substituted hydrophilic moiety (e.g., 2',6'-Dimethyl-4'-(N-succinimidyloxycarboxnyl)phenyl 10-(3'-Sulfopropyl)-acridinium-9-carboxylate (NSP-DMAE-NHS)) is capable of generating about 1.5 times higher chemiluminescent quantum yield as compared to the corresponding PAAE with simple alkyl substitution at the same position (e.g., 2',6'-Dimethyl-4'-(N-succinimidyloxycarbonyl)phenyl 10-Methyl-9-acridinecarboxylate Methylsulfate (DMAE-NHS)). (See Table I). The increase in chemiluminescent quantum yield of PAAE is a very desirable and essential factor in improving the signal to noise (S/N) ratio of the chemiluminescent tracers and the sensitivity of chemiluminescent binding assays and detection schemes. In particular, where the signal enhancement of the tracer is mediated through multiple PAAE labelling of a conjugate of ligand/carrier biomolecule such as a protein, a 1.5 fold or greater improvement in PAAE chemiluminescent quantum yield will mean that less PAAE is required to be bound to achieve the same signal amplitude. Also, if the same levels of binding of PAAE to carrier conjugates is achieved, the detection of lower concentrations of an analyte may be possible.

TABLE I

Relative Quantum Yield of DMAE-NHS vs. NSP-DMAE-NHS

| AE Type | Mol. Wt. | RLU/4.2 fmol AE | RLU Ratio |
| --- | --- | --- | --- |
| DMAE-NHS | 595 | 690,187 | 1.0 |
|  |  | 644,587 |  |
|  |  | 743,587 |  |
|  | mean | 692,787 |  |
|  | SD | 49,551 |  |
|  | % C.V. | 7.2 |  |
| NSP-DMAE-NHS | 591 | 1,122,017 | 1.7 |
|  |  | 1,204,017 |  |
|  |  | 1,122,017 |  |
|  | mean | 1,149,350 |  |
|  | SD | 47,343 |  |
|  | % C.V. | 4.1 |  |

In table I, DMAE-NHS was dissolved in acetonitrile, while NSP-DMAE-NHS in 50% (v/v) acetonitrile in water to generate stock solutions of 1.0 mg/ml. Serial dilutions were carried out to $10^{-7}$ with flashing buffer (10 mM Phosphate, 150 mM NaCl, 0.1% BSA, 0.05% NaN$_3$, pH 8.0) diluent. The dilution method consists of three 100-fold dilution steps using 50 uL transfer volumes and on 10-fold dilution step using 100 uL transfer volume. The light emission of the samples were determined on Ciba Corning Diagnostics MLA1 Analyzer under standard conditions (2 sec light collection time) using 25 uL of the $10^{-7}$ dilution solutions.

There are many modifications which one with ordinary skill in the art will recognize are within the scope of the instant specification. A number of spacers can be attached which will facilitate the connection of the hydrophilic group to the nitrogen atom at the acridinium nucleus, and an electrophile or leaving group that will facilitate the covalent attachment of a hydrophilic PAAE to other compounds or biomolecules.

The novel acridinium esters of the present invention are highly soluble in water and can be encapsulated in liposomes at high concentrations. Once inside liposomes at high concentrations, the novel acridinium esters remain encapsulated for extended periods of time and do not leak appreciably.

It will be appreciated that while the novel acridinium esters of the present invention are useful for encapsulation within liposomes, the novel acridinium esters of the present invention are also useful in other applications where acridinium esters are utilized, such as labeling ligands or analytes (such as antigens); labeling the specific binding partners of ligands or analytes (such as the corresponding antibodies); or labeling nucleic acids and molecules comprising nucleic acids.

In particular, the novel functionalized hydrophilic acridinium esters of the present invention will be useful for labeling biological materials for chemiluminescent assays where it is preferable to reduce the non-specific binding of tracer to biological material. The novel functionalized hydrophilic acridinium esters of the present invention will allow for a reduction in signal/noise (S/N ratio) interference, which will allow for greater accuracy in making measurements and for diagnostic assays, since the hydrophilic nature of the novel compounds of the instant invention will be less prone to non-specific interactions in comparison with other chemiluminescent compounds.

Figure 2:
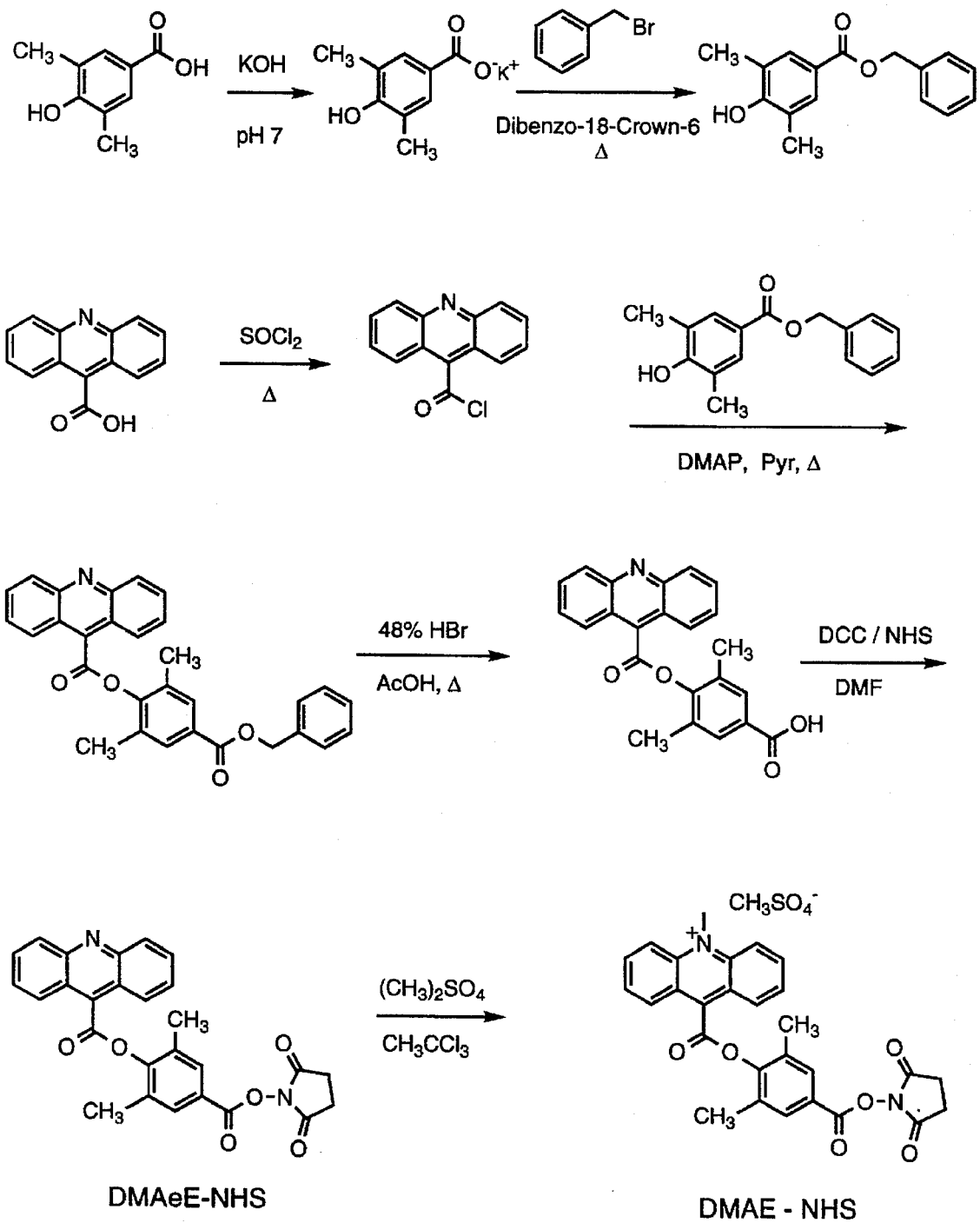
FIG. 2 is a diagram illustrating the old method of synthesis of DMAE-NHS.

Synthesis of acridinium esters have been described as in U.S. Pat. No. 4,745,181 and the process is shown in FIG. 2. This method involved the use of a phenoxy group substituted with a benzyloxycarbonyl group to form the acridine ester. The desired succinimidyloxycarbonyl was then introduced through the removal of the benzyl protecting group and the condensation of the product with N-hydroxysuccinimide in the presence of dicyclohexylcarbodiimide.

In addition, the instant invention provides for a new and improved method of synthesis. This method takes advantage of the unexpected discovery that the acridine nucleus, under properly selected conditions, can be directly condensed with the phenoxy group carrying succinimidyloxycarbonyl, without any problem, this is illustrated in FIG. 1. By using this new and simpler process, two synthetic steps of the older process are eliminated, for the preparation of hydrophilic PAAE with the proper electrophilic or leaving group. The generalized reaction scheme of FIG. 1 also applies to the preparation of substituted acridine acid chlorides, such as

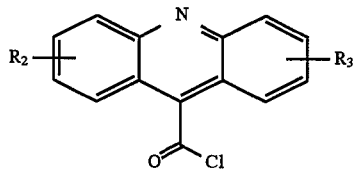

and N-hydroxysuccinimide ester of substituted p-hydroxybenzoates, such as

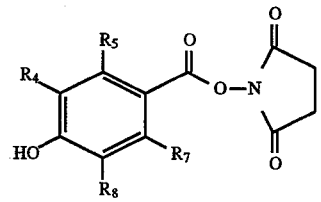

where R2, R3, R5, R7 are hydrogen, halide, nitro, -R, —OR, —CN, —NHCOR, —COR, —COOR, or —CONHR; where R is alkyl, alkenyl, alkynyl, or aralkyl, and where R4 & R8 are R, and R, is as defined above.

Thus the instant invention provides for hydrophilic PAAE with an additional electrophilic or leaving group, which are useful for conjugating with mono- or poly-nucleophilic compounds or biomolecules. The instant invention thus provides for the covalent attachment of the functionalized hydrophilic PAAE with nucleophilic compounds such as hexyl-1,6-diamine, ethylene diamine, and aminocaproic acid. The instant invention also provides for the covalent attachment of the functionalized hydrophilic PAAE with biomolecules such as aminoglycosides, proteins, viral antigens, peptides, and aminoalkyl-functionalized oligonucleotides. These conjugates will be useful for sensitive immunoassays and nucleic acid binding assays. Furthermore, all of the attributes of the instant invention are similarly applicable to related acridinium compounds, including, but not limited to, benzacridinium esters, such as those claimed in copending application Ser. No. 08/035,130.

An example of a useful sensitive chemiluminescent immunoassay utilizing the compounds and conjugates of the instant invention is one which can detect specific steroid hormones in serum samples. An improved assay using the conjugates and methods of the instant invention is a speedy assay for testosterone. This assay combines the use of a highly specific antibody raised to testosterone and a heterologous tracer formed by conjugating a novel C19-mono- or C19-bi-substituted testosterone with a functionalized, hydrophilic PAAE. The benefit of using the heterologous chemiluminescent tracer is observed through the improvement of testosterone assay sensitivity to 0.1 ng/mL, which cannot be otherwise achieved rapidly (ie. about 5 min.) with the use of the corresponding homologous tracer, or using hydrophobic PAAE.

Thus the instant invention also provides for the utilization of functionalized hydrophilic PAAE which were formed as conjugates by novel C19-C-linked type of testosterone derivitization (as described in the Examples to follow). These novel heterologous tracers can be formed, optionally with further olefinic linkage at C19, or additional heteroatom-linked substitution at C19, such as the following C19-O linked derivative of testosterone (NSP-DMAE-HD-19-CMET).

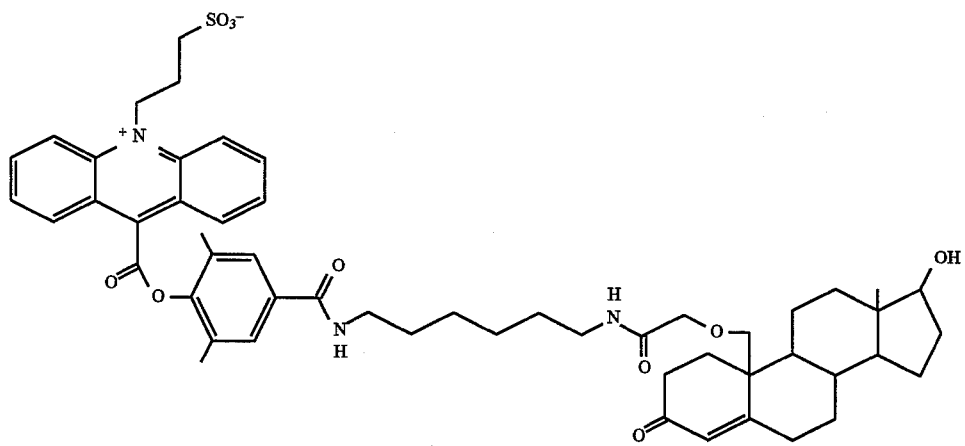

Thus the instant invention also provides for testosterone derivatives of the following structures. (Seven examples are shown below, along with a template identifying the numbering system used for nomenclature.)

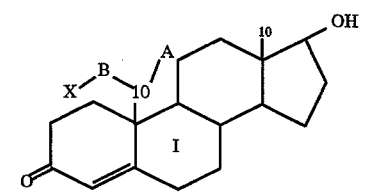

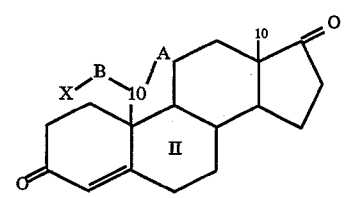

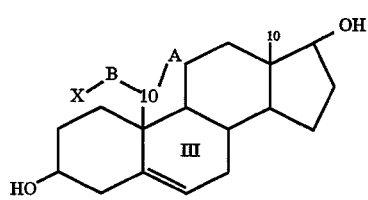

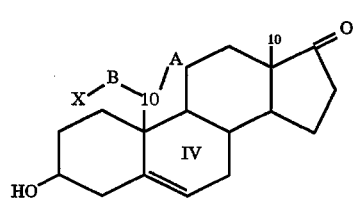

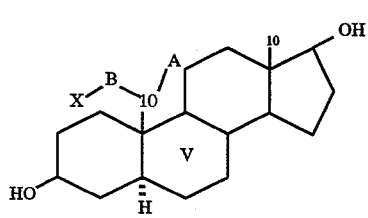

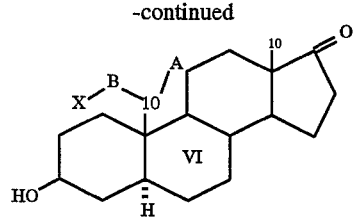

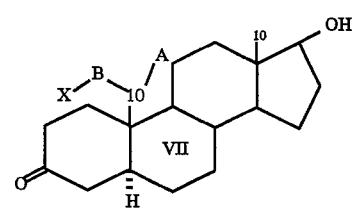

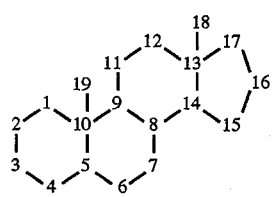

wherein A is a functionalized group selected from the group consisting of —OH, —N($R_1$)$_2$, —NHR$_1$, nitro, halide, —OR$_1$, —OCOR$_1$, -Tosylate, -mesylate, -azide, -isocyanate, -thioisocyanate, —SR$_1$, nitro, —SH, —SSR$_1$, -phosphonate, -sulfonate, —NHCOOR$_1$, —NHCOR$_1$, —NHCONH$_2$, hydrazines, cyanide, and -R$_1$; where R$_1$ is an alkyl, alkenyl, alkynyl, aralkyl containing up to 10 carbons and up to 5 heteroatoms;

where B is —(CH$_2$)$_n$ where n=1-4 or —C≡; when B is —C≡, A is preferably omitted;

where X is a carboxylate, —COOR$_2$, —CONHR$_2$, (where R$_2$ is an alkyl, alkenyl, alkynyl, aryl, aralkyl containing up to 15 carbons and up to 5 heteroatoms), or a carbonyl attached with proper leaving groups, including but not limited to halide, N-hydroxysuccinimide, and imidazole.

The enhanced utility of the hydrophilic PAAE of the instant invention in immunoassay of therapeutic drugs or hormones such as testosterone illustrates one aspect of the invention embodied in the instant specification. Specifically, the use of testosterone derivatives wherein the C19-B linked bridges (as shown in the above figure) are C19-C and an important element to the effective use of the compounds of the instant invention. The use of a C19-C linkage has been found to balance the reduction of tracer binding to the specific anti-testosterone antibody, and the ease of its displacement from antibody by competing sample testosterone.

A preferred embodiment of the testosterone tracers of the instant invention to be utilized for conjugation to the functionalized hydrophilic PAAE, via bifunctional crosslinkers, encompass the forms represented by formula I above. More specifically, it is preferred that A is hydroxy, B is —CH$_2$—, and X is carboxylate.

These compounds are novel, being distinguishable from those known from the prior art. For example, those compounds cited in Rao (U.S. Pat. No. 4,197,286) contain C19-O (i.e., C19 to oxygen) linkages.

Using the teachings of the instant specification one with ordinary skill in the art will recognize the use of bifunctional linkers for conjugation. A preferred embodiment encompasses a functionalized hydrophilic PAAE is attached to n-hexyl-1,6-diamine at one end through the formation of amide linkage, and subsequently to the target biomolecule, such as the testosterone derivative by the formation of another amide linkage with the other end, as exemplified by the following (NSP-DMAE-HD-19-HCMT).

omitted, B is —CH= forming an olefinic linkage with C19, and X is carboxylate, as shown below (NSP-DMAE-HD-19-CVNT).

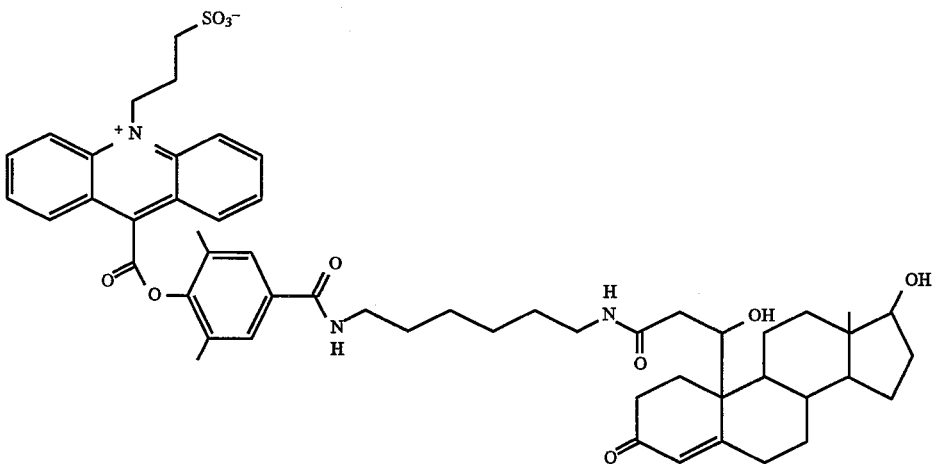

Another preferred embodiment of the testosterone tracer is a form of the compound of formula I above, where A is

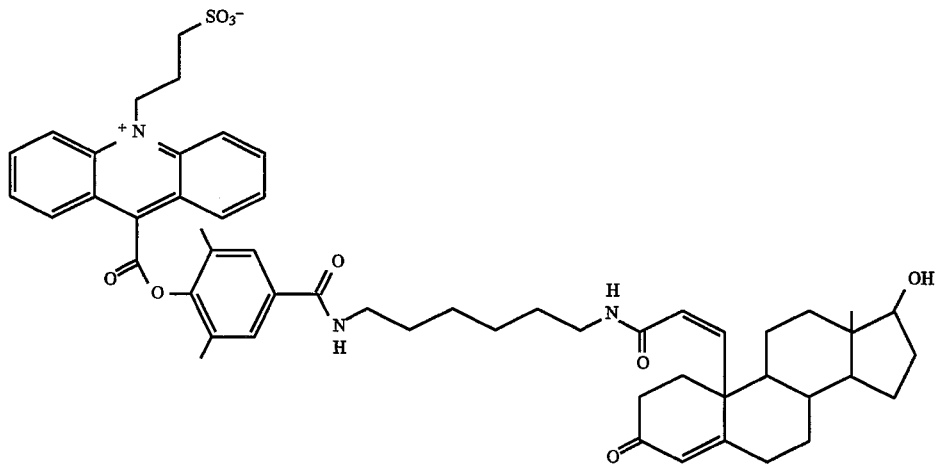

A further aspect of the instant invention encompasses the unexpected improved results of using functionalized hydrophilic PAAE for labeling viral antigen as utilized in various infectious disease chemiluminescent immunoassays. For example, in an IgG capture assay format, where mouse anti-human IgGFc immobilized solid phase and viral antigen tracer are the reagents used for assaying anti-viral antibodies in the serum sample, it was found that great improvement in the signal to noise ratio of the assay can be achieved when a functionalized hydrophilic PAAE is used in place of the conventional DMAE-NHS in preparing the viral antigen tracer. These results most likely occur via better binding activity resulting in enhanced immunocomplex formation between tracer and target antibodies, and lowered non-specific binding due to the use of hydrophilic acridinium ester tags.

Thus one with ordinary skill in the art could take the teachings of the instant invention and apply them to the detection of a variety of infectious agents or pathogens. These infectious agents such as Rubella, Hepatitis of various classes and subtypes, Toxoplasma, Cytomegalovirus (CMV), HIV, chlamidya to name only a few, are targets for early detection which will require assays of great sensitivity and low incidence of false positive indication.

A typical architecture for such an assay consists of, but is not limited to, three components, a tracer, a sample containing the analyte, and a means for partitioning bound from unbound analyte. For example, such assays could combine the functionalized hydrophilic PAAE with suitable antigen of or specific binder for an analyte to form a tracer, incubation with a biological sample (containing the analyte), and capture of the tracer by a solid phase immobilized antibody. Other architectures will become practical with the application of the teachings of the instant invention, and are readily apparent to those with ordinary skill in the art of bioassay.

Figure 9:
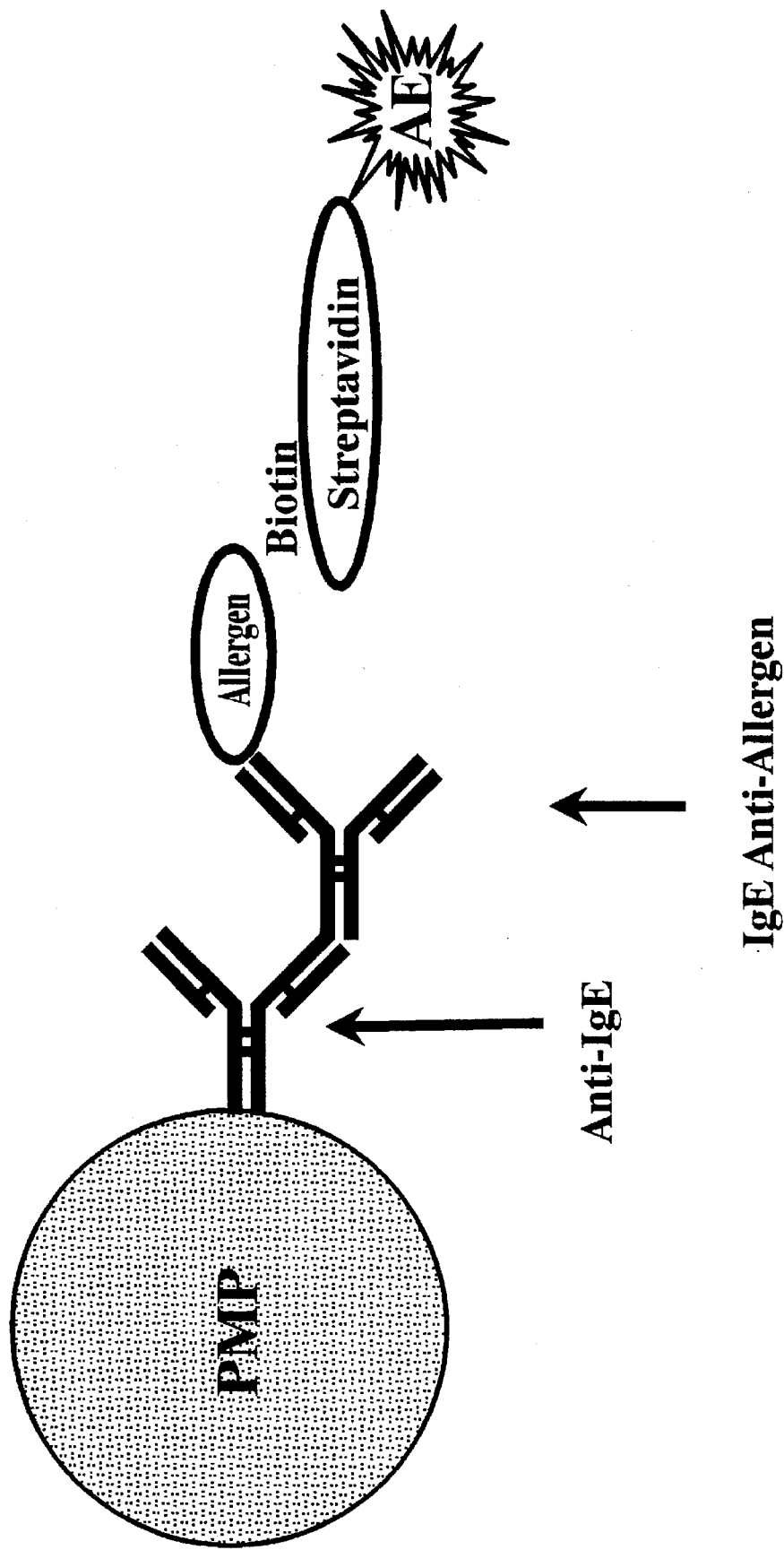
FIG. 9 shows the assay architecture for an ACS allergen assay.

The instant invention encompasses the use of the compositions and methods of the instant invention for allergen immunoassays. The hydrophilic PAAEs of the instant invention will be useful for the detection of specific IgE Ab to specific allergens. In this application, hydrophilic PAAEs are linked to streptavidin, and can be used to detect specific allergen-biotin molecules bound to specific antibodies to the allergen. (See an example for the architecture of an ACS specific IgE assay, FIG. 9.)

Thus the instant invention encompasses methods of measuring the amount of analyte in a sample in and detecting an analyte specifically and in proportion to its concentration in a sample, and measuring a signal which is generated by a hydrophilic acridinium ester chemiluminescent label that is directly or indirectly proportional to the concentration of the analyte in a sample.

Such methods of detecting an analyte in a sample comprise contacting a sample with a hydrophilic acridinium ester labeled detector molecule, sequestering bound detector and analyte, washing away excess detector, and measuring a signal from an analyte bound detector.

Figure 7:
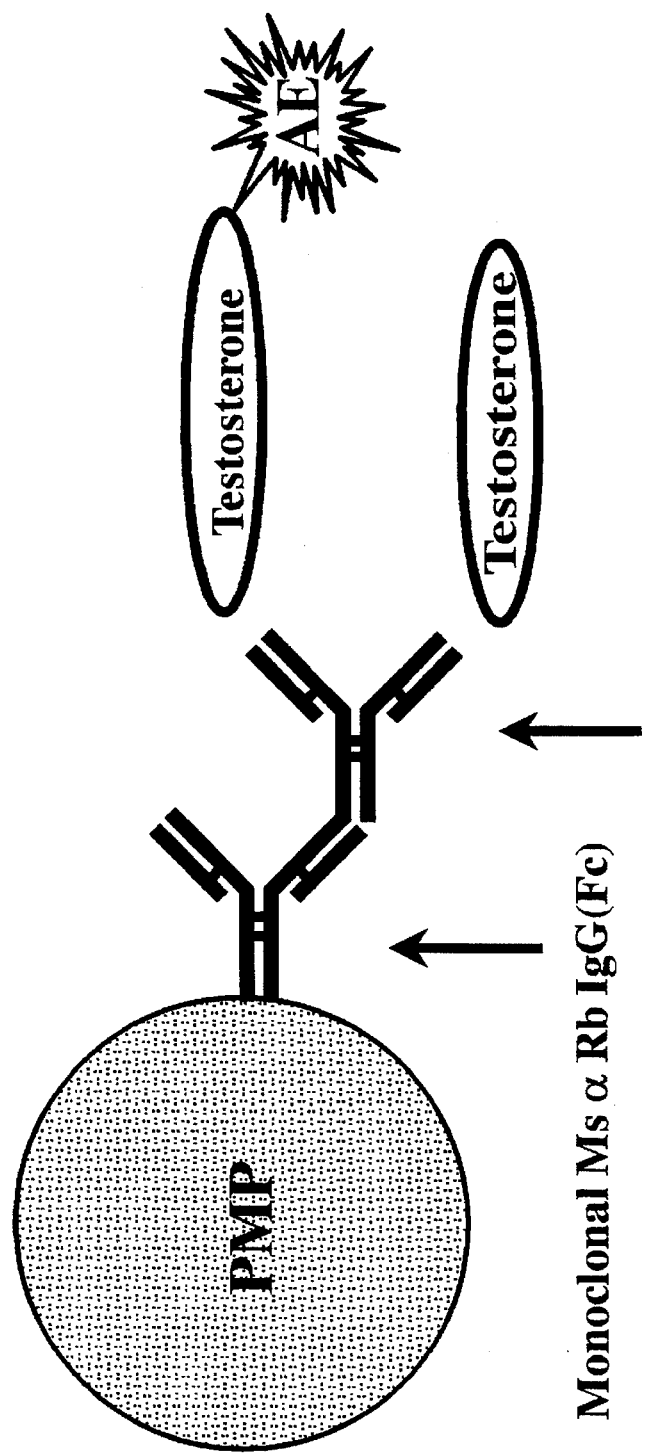
FIG. 7 shows the assay architecture for an ACS Testosterone assay, which is run on the Ciba Corning ACS-180 instrument.

Further, methods of detecting an analyte in a sample comprising, contacting the sample with a hydrophilic acridinium ester labeled competitive tracer, and a specific binder for an analyte, retrieving the specific binder, and determining a signal generated by the bound tracer. (See an example for the assay architecture of an ACS testosterone assay, FIG. 7.) Also encompassed are methods of detecting an analyte in a sample comprising contacting a sample with a hydrophilic acridinium ester labeled competitive tracer, and a specific binder for an analyte, retrieving the specific binder, and determining a signal generated by the unbound tracer.

Included are methods of detecting an analyte in a sample comprising a contacting a sample with a first specific binder, and a second hydrophilic acridinium ester labeled specific binder, and detecting a signal. These assay architectures can be either in the form of sandwich assays or assays in which the second binder (or antibody) is reactive with the first binder. Many variations of these architectures will be apparent to those with ordinary skill in the art.

Figure 8:
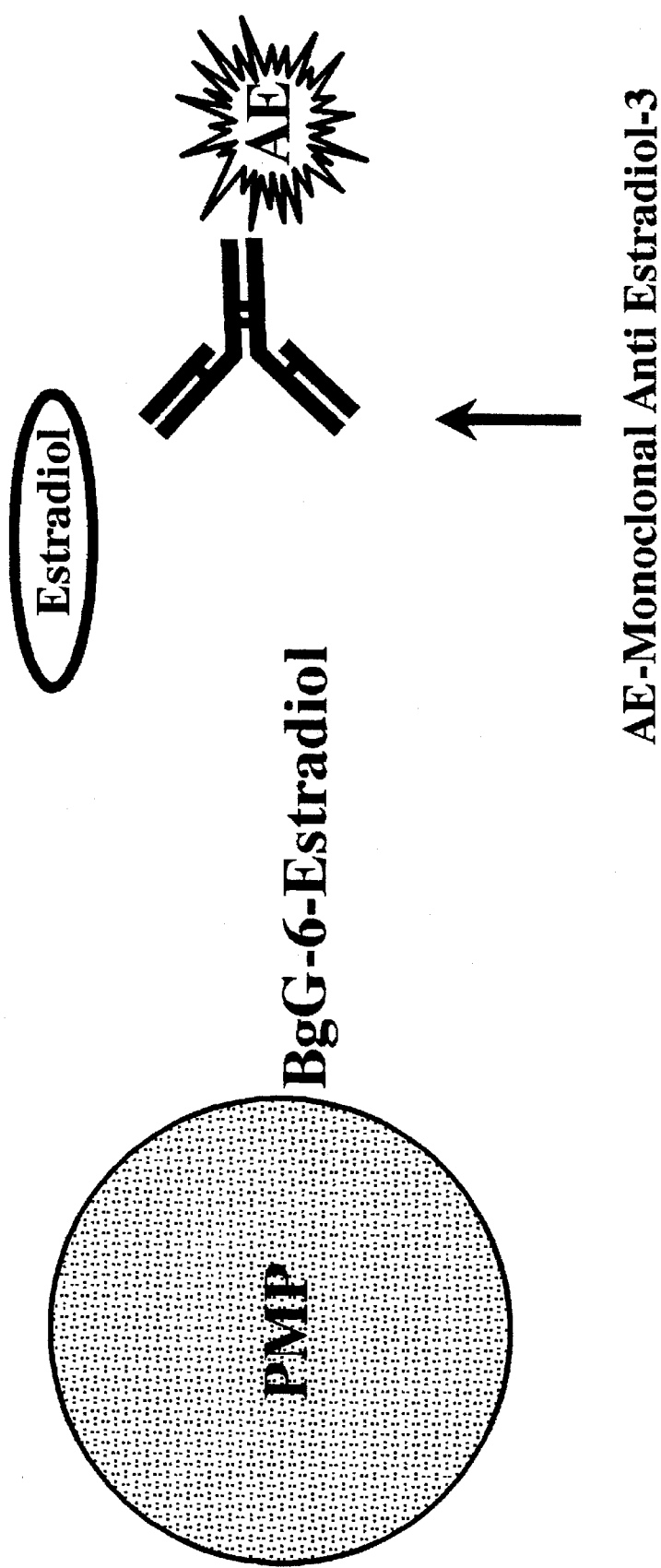
FIG. 8 shows the assay architecture for an ACS Estradiol assay, which is run on the Ciba Corning ACS-180 instrument.

The instant invention encompasses methods of detecting an analyte in a sample comprising a contacting a sample with hydrophilic acridinium ester labelled detector and a competitive binder to the detector, sequestering the detector bound to the competitive binder, washing away excess detector and the detector bound analyte, and measuring a signal from the detector bound to the competitive binder. (See an example for the assay architecture of an ACS estradiol assay, FIG. 8.)

The methods of the instant invention can be practiced with or without the addition of releasing agents prior to detection of a signal, or other agents which will enhance the signal generated.

A further aspect of the instant invention encompasses the use of the compositions and methods of the instant invention for gene probe assays. For example, low level concentration of target nucleic acids (the analyte) can be detected by hybridizing to a first nucleic acid probe, which is conjugated with a macromolecular carrier, such as bovine serum albumin, glycoproteins, etc., labeled with multiple hydrophilic PAAEs and optionally multiple hydrophilic polymers such as polyethylene glycol (PEG), and capturing with a second nucleic acid probe, which is immobilized on a solid phase such as paramagnetic particles. The two nucleic acid probes can be preferentially ligated with ligase after the hybridization step, but prior to the separation step (which removes the unbound probe tracer remaining in the supernatant) to enhance assay specificity. Because of the greater number of PAAE incorporated in the tracer due to the hydrophilic nature, good solubility is maintained. Such nucleic acid detection can be accomplished using several schemes that one with ordinary skill in the art can conceive, and using the teachings of the instant invention, develop the proper hydrophilic PAAE tracers for sensitive detection.

The following examples are presented to illustrate the present invention and are not meant to limit in any way the scope of the instant invention.

EXAMPLE 1A

Improved Synthesis of 2',6'-Dimethyl-4'-(N-succinimidyloxycarbonyl)phenyl 9-acridinecarboxylate (DMAeE-NHS, Precursor of DMAE-NHS and NSP-DMAE-NHS)

Succinimidyl 3,5-dimethyl-4-hydroxybenzoate

A solution of 3,5-dimethyl-4-hydroxybenzoic acid (12.0 g, 72.21 mmol) in 400 mL of anhydrous tetrahydrofuran and 200 mL of anhydrous N,N-dimethylformamide was cooled in an ice-water bath and treated with N-hydroxysuccinimide (8.31 g, 72.21 mmol) with stirring for 15 minutes, followed by addition of dicyclohexylcarbodiimide (17.88 g; 86.65 mmol). After 16 hours of stirring at 25° C. under nitrogen, the mixture was filtered; and the wet cake was washed with 10 mL of anhydrous N,N-dimethylformamide. The combined filtrate was evaporated to dryness under reduced pressure. The residue, after washing with anhydrous diethyl ether (2×50 mL), was suspended in 80 mL of boiling ethyl acetate for 5 minutes. Cooling the suspension to 25° C. gave 11.95 g (63% yield) of the off-white product, which was homogeneous on TLC (Rf 0.6; silica gel, ether).

9-Acridinecarbonyl chloride hydrochloride

A mixture of 9-acridinecarboxylic acid hydrate (10.0 g, 44.80 mmol) in 80 mL of thionyl chloride was refluxed at 100° C. under nitrogen for 2 hours, and then cooled to 25° C. The resulting solution was reduced to about half the original volume under reduced pressure, and then poured into 500 mL of anhydrous diethyl ether. The yellow precipitate was collected, washed with ether (3×100 mL), and dried under reduced pressure for 2 hours, to produce 12.95 g (~100% yield) of the product, which was used immediately for the next reaction.

2',6'-Dimethyl-4'-(N-succinimidyloxycarbonyl) phenyl 9-acridinecarboxylate (DMAeE-NHS)

A solution of succinimidyl 3,5-dimethyl-4-hydroxybenzoate (11.29 g, 42.88 mmol) and 4-dimethylaminopyridine (2.19 g, 17.93 mmol) in 200 mL of anhydrous pyridine was cooled in an ice-water bath, followed by addition of 9-acridinecarbonyl chloride hydrochloride (12.95 g, 44.80 mmol). The solution was heated with stirring under nitrogen at 100° C. for 2 hours, and then at 25° C. for 16 hours. After removal of the solvent under reduced pressure, the residue was flash-chromatographed on a silica gel column (Baker silica gel, Cat#7024-1; F7×50 cm) packed with 50% diethyl ether/hexane, and eluted with 75% diethyl ether/hexane (2.5 L), diethyl ether (2 L), 5% ethyl acetate/diethyl ether (3 L) and 25% ethyl acetate/methylene chloride (5 L). Fractions containing the product (Rf 0.4; silica gel TLC plate, ether), collected from the 25% ethyl acetate/methylene chloride eluent, were combined, and evaporated to dryness under reduced pressure, to collect the light-yellow product (DMAeE-NHS) in 10.03 g (50% yield from 9-acridinecarboxylic acid hydrate).

EXAMPLE 1B

Improved Synthesis of 2',6'-Dimethyl-4'-(N-succinimidyloxycarbonyl)phenyl 10-Methyl-9-acridinecarboxylate Methylsulfate (DMAE-NHS), Using Toluene as Solvent This procedure uses toluene as a solvent in methylation of DMAeE-NHS, to replace the ozone-depleting reagent 1,1,1-trichloroethane, which was previously used as the solvent in the methylation process as described in U.S. Pat. No. 4,745,181.

A suspension of DMAeE-NHS (1.0 g, 2.13 mmol) in 50 mL of anhydrous toluene was heated to 110° C. to give a homogeneous solution, which was cooled to room temperature followed by addition of 11.0 mL (116.25 mmol) of distilled dimethyl sulfate. After 20 hours of stirring at 110° C. under nitrogen, the solution was cooled to room temperature, and then at 4° C. for 1 hour. The mixture was filtered, and the yellow wet cake was washed with toluene (2×5 mL) followed by anhydrous methylene chloride, heated to boiling for 2-3 minutes, and filtered. The volume of filtrate was reduced to about 50 mL on a hot plate. Cooling the concentrate to room temperature gave yellow crystals, which were collected and washed with diethyl ether (3×20 mL), to afford 500 mg (39%) of the pure product. FAB/MS (483, M+).

EXAMPLE 2

Synthesis of 2',6'-Dimethyl-4'-(N-succinimidyloxycarboxnyl)phenyl 10-(3'-Sulfopropyl)-acridinium-9-carboxylate (NSP-DMAE-NHS)

DMAeE-NHS (500 mg, 1.07 mmol) and 1,3-propane sultone (6.5 g, 53.3 mmol) were heated at 150° C. under nitrogen in a sealed tube for 20 h. After cooling, excess 1,3-propane sultone was removed by trituration with toluene (3×5 mL). The crude product was purified by RP-HPLC using a C18, 30×500 mm, 10 μm, preparative column, and eluted with a mixture of 65% solvent A and 35% solvent B. Conditions: solvent A: 0.05% (v/v) TFA/H$_2$O, solvent B: 0.05% (v/v) TFA/CH$_3$CN; flow rate 25 mL/min; UV detection at 260 nm. The product was eluted at 26.8 min; yield: 60 mg (25%); FAB/MS (591, M+H).

EXAMPLE 3

Synthesis of 19-Carboxymethyl-17B,19-dihydroxy-4-androsten-3-one (19-Hydroxy-19-carboxymethyl-testosterone, 19-HCMT)

3,17-Bis(ethylenedioxy)-19-ethoxycarbonylmethyl-19-hydroxy-5-androstene

A 50 mL 2-neck flask equipped with a rubber septum, magnetic stirring bar and N$_2$ inlet was charged with lithium bis(trimethylsilyl)amide (12.9 mL of 1.0M solution, 12.9 mmol). The solution was cooled to −78° C. under N$_2$ in dry ice-acetone bath and anhydrous ethyl acetate (1.2 mL, 12.9 mmol) was added dropwise from a syringe. The reaction was stirred at −78° C. for 30 minutes and then a solution of 3,17-bis(ethylenedioxy)-5-androsten-19-al (1 g, 2.58 mmol) (Lovett, J. A. et al., 1984, J. Med. Chem. 27:734–740) in anhydrous tetrahydrofuran (15 mL) was added dropwise to the solution of the enolate. After completion of the addition, the reaction was stirred for an additional 1.5 hours in the dry ice-acetone bath under nitrogen. The reaction was then quenched with the addition of saturated ammonium chloride solution (~30 mL) and the resulting suspension was extracted three times with ethyl acetate (3×25 mL). The combined ethyl acetate extract was washed once with brine (~30 mL) and was then dried over magnesium sulfate. After filtration, the solvent was removed under reduced pressure to yield an oil which was used as such in the next reaction: yield 1.67 g (crude); mass spectrum (chemical ionization) m/z 477 (M+H+).

3,17-Dioxo-19-ethoxycarbonylmethyl-19-hydroxyl-5-androstene

The crude bisketal from above (1.67 g) was dissolved in tetrahydrofuran (20 mL) and 3N perchloric acid (10 mL) was added. The reaction was stirred at room temperature for 3 hours and was then diluted with water (40 mL). The resulting suspension was extracted twice with ethyl acetate (2×40 mL). The combined ethyl acetate extract was washed once with water (~40 mL) and was then dried over magnesium sulfate. After filtration, the solvent was removed under reduced pressure to afford the crude product which was purified by preparative TLC using 1:1 ethyl acetate/hexanes as eluent (Rf=0.17): yield 0.46 g (46% two steps) white foam; mass spectrum (chemical ionization) m/z 389 (M+H+).

19-Ethoxycarbonyl-17B, 19-dihydroxy-4-androsten-3-one

In a 50 mL round bottom flask equipped with a magnetic stirring bar and a nitrogen inlet, was placed 3,17-dioxo-19-ethoxycarbonylmethyl-19-hydroxy-5-androsten (50 mg, 0.129 mmol) and anhydrous methanol (5 mL). The solution of the steroid was stirred and cooled in ice under nitrogen and sodium borohydride (6.4 mg, 0.168 mmol) was added as a solution in methanol (1 mL). The reaction was stirred in ice for 8 minutes and was then quenched with the addition of acetone (1 mL) and acetic acid (2 mL). The reaction mixture was then diluted with water (~25 mL) and the resulting suspension was extracted with ethyl acetate (~35 mL). The ethyl acetate extract was dried over magnesium sulfate, filtered and then concentrated under reduced pressure to afford a white powder: yield 51 mg (quant.) which was homogenous on TLC (1:19, MeOH/CHCl$_3$) (Rf=0.26). This material was used as such in the next reaction.

19-Carboxymethyl-17b,19-dihydroxy-4-androsten-3-one (19-HCMT)

The ethyl ester from above (51 mg, 0.129 mmol) was dissolved in methanol (5 mL) and treated with KOH (0.25 g). The reaction was stirred at room temperature for 1 hour and was then quenched with the addition of water (25 mL) and acetic acid until the pH of the solution was adjusted to 6. The resulting mixture was further acidified with the addition of 0.5N HCL (1 mL) and the resulting suspension was extracted three times with ethyl acetate (3×15 mL). The combined ethyl acetate extract was dried over magnesium sulfate, filtered and concentrated. The crude acid was purified by preparative TLC using 2% acetic acid in ethyl acetate as eluent (Rf=0.4) and was isolated as a white powder. yield: 10 mg (22%); mass spectrum (chemical ionization) 363 (M+H+).

EXAMPLE 4

Synthesis of 10-Carboxyvinyl-17B-hydroxy-19-nor-4-androsten-3one (19-Carboxyvinyl-nor-testosterone; 19-CVNT)

3,17-Bis(ethylenedioxy)-10-ethoxycarbonylvinyl-19-nor-5-androstene

A 50 mL 2-neck flask equipped with a magnetic stirring bar, reflux condenser with a nitrogen inlet and a rubber septum was charged with triethylphosphonoacetate (0.35 g, 1.7 mmol) and anhydrous tetrahydrofuran (5 mL). The solution was cooled in an ice-salt bath to ~−10° C. under nitrogen and n-butyl lithium (1.24 mL of 1.6M solution, 1.7 mmol) was added. The reaction was stirred at −10° C. for 30 minutes and then a solution of 3,17-bis(ethylenedioxy)-5-androsten-19-al (0.22 g, 0.57 mmol) in anhydrous tetrahydrofuran (5 mL) was added dropwise from a syringe. The reaction was then warmed to room temperature and was then refluxed under nitrogen for 24 hours. After cooling to room temperature, the reaction mixture was then partitioned between a 1:1 mixture of water and ethyl acetate. The ethyl acetate layer was separated and washed with brine. It was then dried over magnesium sulfate, filtered and concentrated under reduced pressure. The residue was purified by preparative TLC using 2:3, ethyl acetate/hexanes as eluent (Rf=0.34) and was isolated as a white fluffy solid: yield 0.11 g (43%); mass spectrum (chemical ionization) 459 (M+H+).

3,17-Dioxo-10-ethoxycarbonylvinyl-19-nor-4-androstene

A solution of the bisketal (0.11 g) from above in acetone (10 mL) was treated with p-toluenesulfonic acid (20 mg). The reaction was stirred at room temperature for 16 hours and was then concentrated under reduced pressure. The resulting residue was partitioned between ethyl acetate and water. The ethyl acetate layer was separated, dried over magnesium sulfate and then concentrated under reduced pressure. The product was purified by preparative TLC using 1:1, ethyl acetate/hexanes as eluent (Rf=0.51) and was isolated as a white powder yield 20 mg (23%). This material was used as such for the next reaction.

10-Ethoxycarbonylvinyl-17b-hydroxy-19-nor-4-androsten-3-one

A solution of 3,17-dioxo-10-ethoxycarbonylvinyl-19-nor-4-androstene (19.5 mg, 0.053 mmol) in methanol (3 mL) was cooled in ice under nitrogen and was treated with sodium borohydride (2.7 mg). The reaction was stirred in ice under nitrogen for 30 minutes and was then quenched with the addition of acetone (1 mL) and acetic acid (1 mL). The resulting solution was concentrated and the residue was partitioned between ethyl acetate and water. The ethyl acetate layer was separated, dried over magnesium sulfate, filtered and then concentrated under reduced pressure. The residue obtained (19 mg) was dissolved in anhydrous chloroform (5 mL) and treated with activated MnO$_2$ (100 mg). The black suspension was stirred at room temperature under nitrogen 30 minutes and was then diluted with ethyl acetate and filtered. The filtrate was concentrated under reduced pressure to afford a white powder which was homogenous on TLC (1:19, methanol/chloroform, Rf=0.28): yield 18.2 mg (92%).

10-Carboxyvinyl-17B-hydroxy-19-nor-4-androsten-3-one (19-Carboxyvinyl-nor-testosterone; 19-CVNT)

A solution of 10-ethoxycarbonylvinyl-17B-hydroxy-19-nor-4-androsten-3-one (17 mg) in methanol (3 mL) was treated with 5% KOH (2 mL). The reaction was stirred at room temperature for 30 minutes and was then acidified with 1N HCL. The resulting suspension was extracted twice with ethyl acetate (2×25 mL). The combined ethyl acetate extract was dried over magnesium sulfate, filtered and concentrated under reduced pressure to afford a white powder which was homogenous on TLC (2% acetic acid in ethyl acetate, Rf=0.25): yield 15.2 mg (97%); mass spectrum (chemical ionization) 345 (M+H+).

EXAMPLE 5

Synthesis of NSP-DMAE/19-HCMT Conjugate Cross-linked with n-Hexyl-1,6-diamine (NSP-DMAE-HD-19-HCMT)

First, NSP-DMAE-NHS was crosslinked with n-hexyl-1,6-diamine to yield NSP-DMAE-HD. Thus, to a yellow solution of NSP-DMAE-NHS (60 mg, 0.1 mmol) in anhydrous DMF/CH$_3$OH (1:4, 10 mL) was added n-hexyl-1,6-diamine (116.2 mg, 1 mmol). The resulting colorless solution was stirred at room temperature under nitrogen for 15 hours, and concentrated to ~1 mL. The crude product was purified by TLC using a preparative silica gel plate (2000 mm, 20×20 cm) developed with "CHCL$_3$"/CH$_3$OH/H$_2$O (55/40/5). The product had Rf=0.5; yield: 50.2 mg (84%); FAB/MS (593, M+H).

Subsequently, a solution of 19-hydroxy-19-carboxymethyl-testosterone (19-HCMT, 4 mg, 0.011 mmol) in anhydrous DMF (0.1 mL) was diluted with anhydrous CHCL$_3$ (0.4 mL), cooled in an ice-bath, and activated with a solution of DCC (2.7 mg, 0.013 mmol) in anhydrous CHCL$_3$ (0.1 mL). The reaction mixture was stirred at 0° C. for 10 minutes, followed by the addition of NSP-DMAE-HD (6 mg, 0.01 mmol) in anhydrous DMF (0.2 mL) and the new reaction mixture was stirred at room temperature for 15 hours. The crude product was purified by RP-HPLC using a C18, 7.8×300 mm, 10 μm, semipreparative column, solvent A: 0.05% (v/v) TFA/H$_2$O, solvent B: 0.05% (v/v) TFA/CH$_3$CN, flow rate: 2.5 mL/min, UV detection at 260 nm. Initially 30% solvent B was used for 15 minute followed by a linear gradient to 50% solvent B in 5 min. The product was eluted at 24.5 minutes; yield: 2.3 mg (25%); FAB/MS (936, M+H).

EXAMPLE 6

Synthesis of NSP-DMAE/19-CVNT Conjugate Cross-linked with n-Hexyl-1,6-diamine (NSP-DMAE-HD-19-CVNT)

NSP-DMAE-HD-19-CVNT was prepared from 19-CVNT (2 mg, 0.006 mmol) and NSP-DMAE-HD-19-CVNT (3 mg, 0.005 nmol) as described in example 5. The crude product was purified by RP-HPLC using a C18, 7.8×300 mm, semipreparative column. Initially 30% solvent B was used for 15 minutes followed by a linear gradient to 60% solvent B in 5 minutes, where solvent A: 0.05% (v/v) TFA/H$_2$O and solvent B: 0.05% (v/v) TFA/CH$_3$CN; flow rate 2.5 mL/min; UV detection at 260 nm. The product was eluted at 23.2 minutes. Product yield: 0.72 mg (16%); FAB/MS (918, M+H)–

EXAMPLE 7

Synthesis of NSP-DMAE/Testosterone-19-CME Conjugate Cross-linked with n-Hexyl-1,6-diamine (NSP-DMAE-HD-19-CMET)

NSP-DMAE-HD-19-CMET was prepared from testosterone-19-CME (4 mg, 0.011 mmol) and NSP-DMAE-HD (3 mg, 0.005 mmol) as described in example 5. The crude reaction mixture was first separated on a preparative TLC plate (silica gel, 1000 μm, 20% MeOH/CH$_2$Cl$_2$) Two bands at Rf 0.2 and Rf 0.3 were collected, combined and further purified by RP-HPLC using a C18, 10 μm 7.8×300 mm, 10 mm, semipreparative column. Initially 30% solvent B was used for 15 minutes followed by a linear gradient to 60% solvent B in 5 minutes, where solvent A: 0.05% (v/v) TFA/H$_2$O and solvent B: 0.05% (v/v) TFA/CH$_3$CN; flow rate 2.5 mL/min; UV detection at 260 nm. The product was eluted at 24.1 minutes. Product yield: 0.3 mg (6.4%); FAB/MS (936, M+H).

EXAMPLE 8

Synthesis of DMAE/19-HCMT conjugate cross-linked with n-hexyl-1,6-diamine (DMAE-HD-19-HCMT)

First, DMAE-NHS was derivatized with n-hexyl-1,6-diamine to yield DMAE-HD as described in Example 5. Thus to a yellow solution of DMAE-NHS (50 mg, 0.084 mmol) in anhydrous DMF/CH$_3$OH (1:4, 10 mL) was added n-hexyl-1,6-diamine (98 mg, 0.84 mmol). The resulting solution was stirred at room temperature under nitrogen for about 4 hours and evaporated. The crude product was purified by TLC using preparative silica gel plates (2000 mm, 20×20 cm) developed with CHCl$_3$/CH$_3$OH/H$_2$O (65/25/4). The product band at Rf=0.4 was stripped, eluted with the same solvent system. The eluent was evaporated to a residue which was triturated with chloroform, filtered and the filtrate evaporated to give purified DMAE-HD (20 mg, 41%).

DMAE-HD-19-HCMT was prepared from 19-HCMT (4.75 mg, 0.013 mmol) and DMAE-HD (7 mg, 0.012 mmol) as described in Example 5. One third of the crude product was purified by RP-HPLC using a C18, 10 μm 7.8×300 mm, semipreparative column. Initially 30% solvent B was used for 15 minutes followed by a linear gradient to 60% solvent B in 5 minutes, where solvent A: 0.1% (v/v) TFA/H$_2$O and solvent B: 0.1% (v/v) TFA/CH$_3$CN, flow rate 2.3 mL/min; UV detection at 260 nm. The product was eluted at 23 min. Product yield: 1.5 mg (45%); FAB/MS (828.5 M+).

EXAMPLE 9

Assay for Testosterone

This example teaches a sensitive and rapid competitive chemiluminescence immunoassay for testosterone using the hydrophilic NSP-DMAE-HD-19-HCMT tracer, that is heterologous to the antibody immunogen at the bridge. The data shows the clear advantage of this new hydrophilic tracer compared to the conventional hydrophobic DMAE-HD-19-HCMT tracer by allowing the development of a rapid, high sensitivity testosterone assay.

A) Production and Characterization of Polyclonal and Monoclonal Antibodies:

Commercially available, rabbit polyclonal antibodies that are anti-testosterone-19-o-carboxymethylether-Human Serum Albumin (RAT-19), was purchased from OEM, (Tom's River, N.J.). The production of this antibody was previously described by Rao (U.S. Pat. No. 4,197,286). A mouse monoclonal antibody against rabbit IgG was produced by a modified version of the technique described by Kohler and Milstein (Nature (London) 256, 495–497 (1975)). Mice were immunized with purified rabbit IgG to produce a mouse monoclonal anti-rabbit IgG (MAR-IgG). Standard antibody screening techniques were used to select a hybridoma with high specificity for rabbit IgG. Ascites was produced using clone HMF1-11B5-3F1-5H7.MAR-IgG antibody was purified from the ascites using Protein A-sepharose (Pharmacia Fine Chemicals, Piscataway, N.J.) affinity chromatography.

B) Development of a Testosterone Chemiluminescence Immunoassay

Optimal assay performance for a rapid testosterone chemiluminescence assay was achieved with the MAR-IgG (described above) covalently coupled to a solid phase and preincubated with the RAT-19 antibody using the NSP-DMAE-HD-19-HCMT as the tracer. The assay used paramagnetic particles (PMP) (Advanced Magnetics Inc., Cambridge, Mass.) as the solid phase.

The MAR-IgG (160 mg per gram of PMP) in 0.1M sodium phosphate, pH 7.4, was covalently linked to the PMP after activation of the PMP with 0.5% glutaraldehyde in 0.1N sodium phosphate (method modified from Groman et al., 1985, BioTechniques 3, 156–160). This was followed by incubation with RAT-19. Excess RAT-19 was removed by additional washes of the reaction mix with phosphate buffer.

Figure 3:
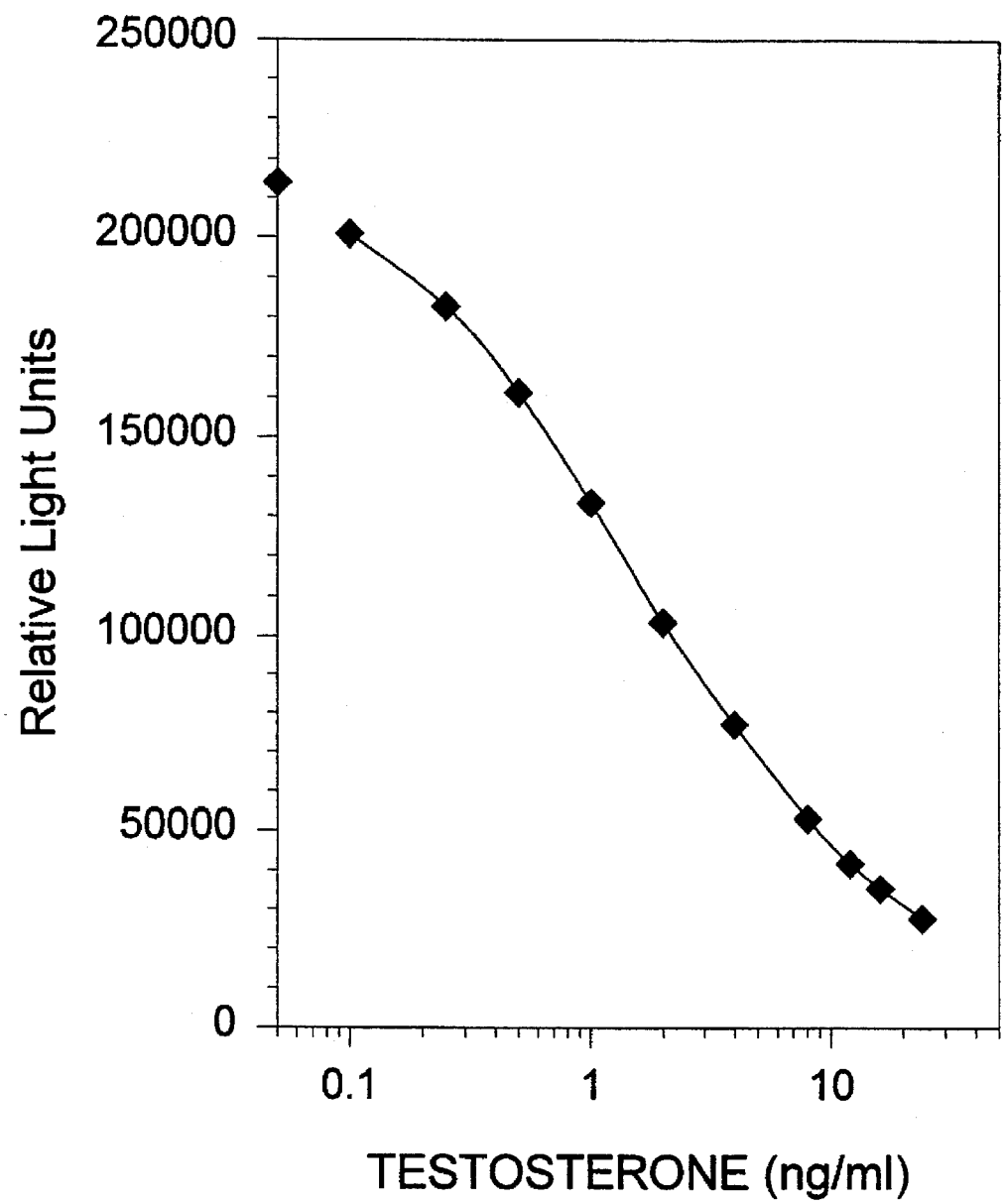
FIG. 3 is a standard curve for a testosterone immunoassay using the compounds of the instant invention.

Twenty-five microliters (mL) of a serum sample or testosterone standard (0.1 to 24 ng/mL or 2.5 to 600 pg/tube), 50 mL of NSP-DMAE-HD-19-HCMT tracer (6×10$^6$ Relative Light Units/test) and 300 mL of MAR-IgG/RAT-19 antibody-solid phase were added simultaneously, incubated at 37° C. for 5 minutes, washed and the chemiluminescence measured on an ACS:180 (Ciba Corning Diagnostics, Medfield, Mass.) automated chemiluminescence immunoassay system. The chemiluminescence signal (Relative Light Units) is inversely proportional to the testosterone concentration. Assay standards consisted of pure testosterone in steroid-free, charcoal stripped human plasma. The testosterone standard binding curve (percent of RLU of standard to RLU of zero standard) for the described assay is shown in FIG. 3. Testosterone doses from serum samples were generated on the ACS:180 using two point calibration off a master curve. Three other testosterone tracers, namely, NSP-DMAE-HD-19-CVNT (heterologous to the antibody immunogen), NSP-DMAE-HD-19-CMET (homologous to the antibody immunogen), and DMAE-HD-19-HCMT (a non-hydrophilic version of the NSP-DMAE-HD-19-HCMT) were evaluated in the same assay format for their effect on the binding curve and the 50% maximum binding (ED50) of the standard binding curve. The DMAE-HD-19-HCMT tracer was evaluated to demonstrate the advantage of employing a hydrophilic PAAE (NSP-DMAE) tag versus a hydrophobic PAAE tag (DMAE).

C) Conventional Radioimmunoassay for Testosterone

The results (n=145) of a conventional testosterone radioimmunoassay ($^{125}$Iodine) were compared in selected male and female serum samples with the ACS:180 chemiluminescence assay using the heterologous testosterone tracer, NSP-DMAE-HD-19-HCMT. The Coat-A-Count Total Testosterone (DPC, Los Angeles, Calif.) commercial system was used. This assay has a three hour incubation time with a 50 mL sample size. The reported minimum detectable dose is approximately 2 picograms per tube as calculated from the manufacturers package insert V116 dated Jan. 27, 1992. This assay was performed according to the manufacturer's instructions.

D) Competitive Chemiluminescence Assay

Figure 5:
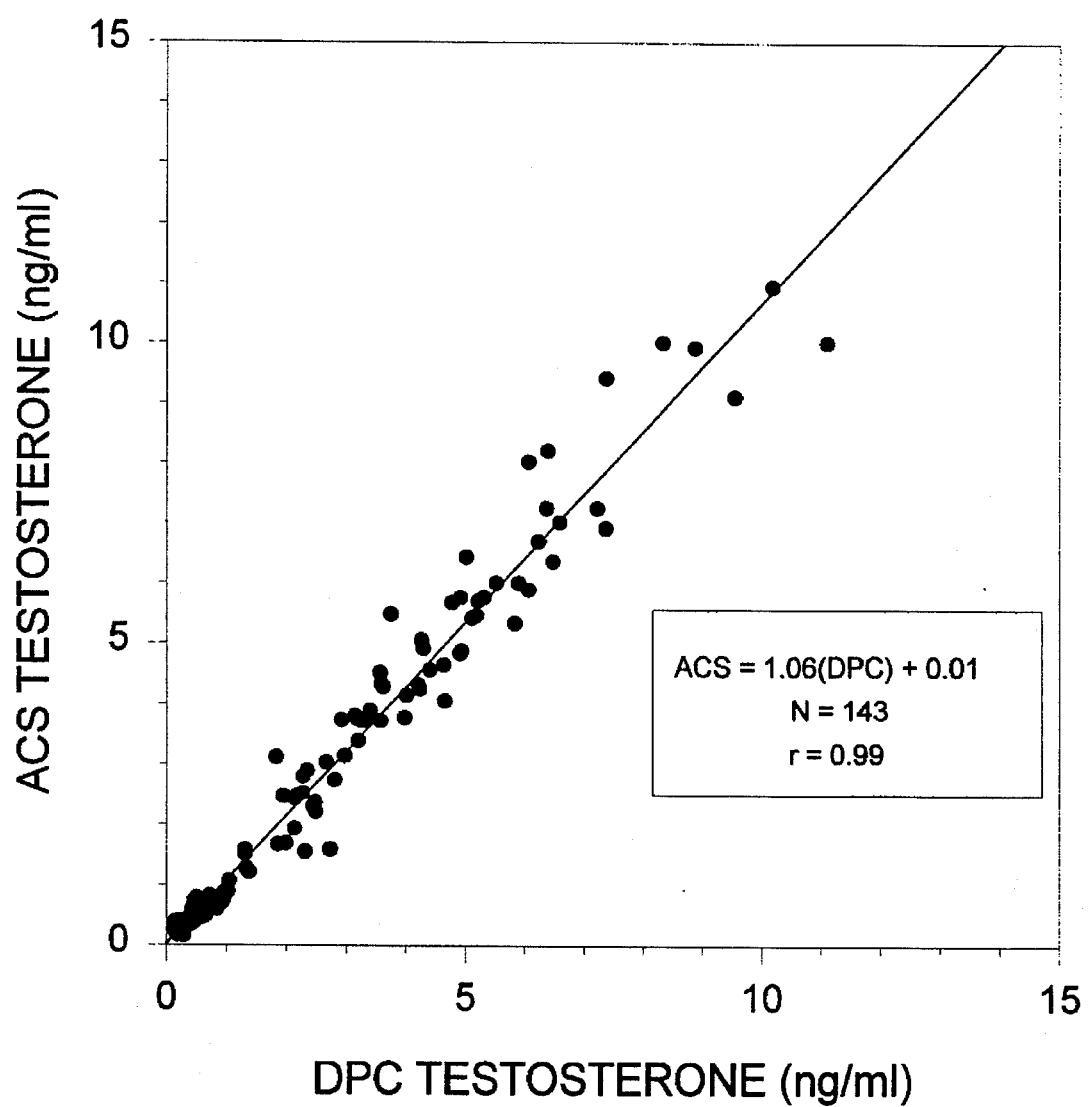
FIG. 5 is plot showing the correlation of results from a testosterone immunoassay using the compounds of the instant invention with DPC Coat-a-Count radioimmunoassay (Diagnostic Products Corp., Los Angeles, Calif.)

The minimum detectable dose (Rodbard, 1978 Anal. Biochem. 90, 1–12) of the rapid automated testosterone immunoassay using the heterologous testosterone tracer NSP-DMAE-HD-19-HCMT is 1.25 pg/tube, a 1.6 fold increase over the conventional 3 hour radioimmunoassay method described above. As shown in FIG. 5, patient sample results for the chemiluminescent assay correlate very well to the radioimmunoassay. The crossreactivity profile of the assay is shown in Table 2. These data suggest that the new chemiluminescent assay is of useful value in the analytical determination of testosterone in human serum samples.

TABLE 2

Specificity of ACS Testosterone chemiluminesence immunoassay using NSP-DMAE-HD-19-HCMT tracer

| Cross-reactant | Dose | % Cross-reactivity | Specifications % |
| --- | --- | --- | --- |
| Androstenedione | 100 ng/mL | 1.55 | <1 |
| Androsterone | 1 ug/mL | 0.03 | <0.1 |
| Cortisol | 1 ug/mL | 0.03 | <0.1 |
| Corticosterone | 1 ug/mL | 0.02 | <0.1 |
| 11-deoxycortisol | 1 ug/mL | 0.05 | <0.1 |
| 5a-dihydrotestosterone | 100 ng/mL | 8.3 | <15 |
| Estradiol-17B | 100 ng/mL | 0.12 | <0.1 |
| Estrone | 100 ng/mL | 0.07 | <0.1 |
| Progesterone | 1 ug/mL | 0.09 | <0.1 |
| Danazol | 1 ug/mL | 0.06 | <0.1 |
| Dexamethasone | 1 ug/mL | 0.01 | <0.1 |

Figure 4:
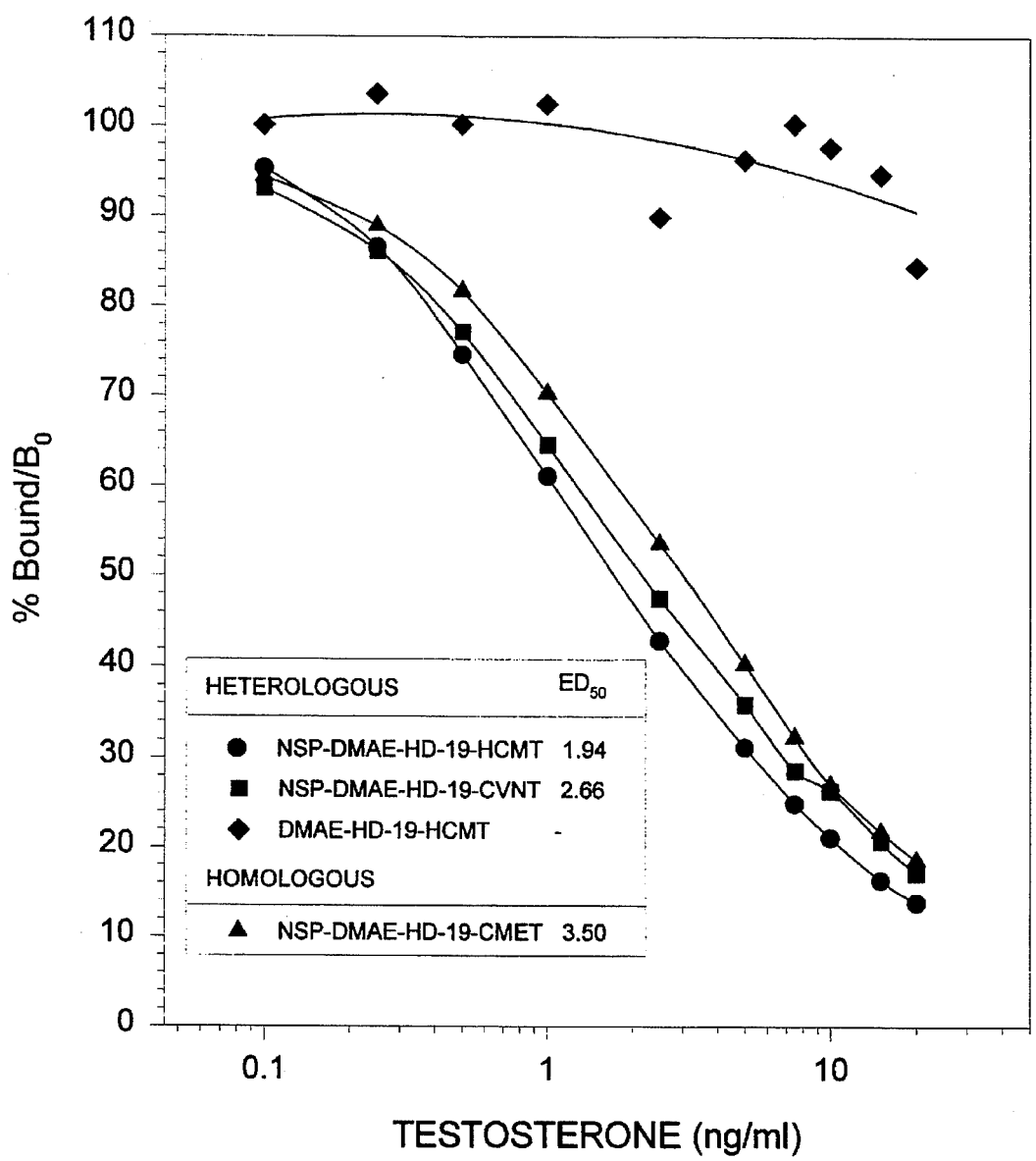
FIG. 4 is a comparison of binding curves for heterologous and homologous tracers in a chemiluminescence immunoassay for testosterone using the compounds of the instant invention. The figure also shows a comparison between using hydrophilic vs. non-hydrophilic acridinium esters.

A comparison of the standard binding curves and calculated ED50's for each chemiluminescent tracer under the same conditions are shown in FIG. 4. The highest ED50 is for the NSP-DMAE-HD-19-CMET tracer that is homologous to the antibody immunogen. The ED50's, for both heterologous tracers, NSP-DMAE-HD-19-CVNT and NSP-DMAE-HD-19-HCMT, are lower than for the homologous tracer indicating that the heterologous tracers are more easily displaced by testosterone than the homologous tracer. Little displacement is seen with the hydrophobic DMAE-HD-19-HCMT tracer indicating the clear advantage of the hydrophilic NSP-DMAE-HD-19-HCMT version of the tracer in testosterone immunoassay.

EXAMPLE 10

Rubella IgG Capture Assay

A rubella IgG capture assay was used to evaluate NSP-DMAE-NHS and DMAE-NHS as reagents for the direct labelling of rubella. Intact rubella virus was labeled with either NSP-DMAE-NHS or DMAE-NHS as described below. Both of these tracer preparations were subjected to a titering study and a population study. The performance of each rubella tracer can be determined by analyzing the positive sample/negative sample ratio generated by each tracer for a given sample population. In this rubella IgG capture assay, the Positive signal/Negative signal (P/N) ratio also reflects on the ability to accurately distinguish small differences in the level of rubella specific IgG. The preferred rubella tracer is one that generates appreciable differences in P/N ratios for samples spanning a wide range of IU/mL levels, since this will lead to greater sensitivity in rubella specific IgG detection.

A) Preparation of Rubella Virus Tracers

Rubella virus (grade IV, 1 mL at 0.5 mg/mL) purchased from Viral Antigens, Inc (Memphis, Tenn.) was dialyzed into labelling buffer (10 mM Phosphate, 0.125N NaCl, pH 8) using a centricon-30 microconcentrator (Amicon, Danvers, Mass.). The virus sample was brought to 2 mL volume in labelling buffer, then concentrated 10-fold by spinning the centricon-30 in a tabletop centrifuge for 30 minutes at 2600 rpm. The concentrate was again brought to 2 mL with labelling buffer. This concentration and reconstitution process was repeated 3 times. The sample was then split into 2×1 mL aliquots for use in subsequent labelling procedures.

To each Rubella virus aliquot (0.25 mg in 1 mL buffer) was added NSP-DMAE-NHS (50 µg in 25 µL dimethylformamide) or DMAE-NHS (50 µg in 25 µL dimethylformamide) solution separately. The labelling reaction mix was vortexed briefly and incubated at room temperature for 15 minutes and stopped by adding 5 mg of lysine (Sigma, St. Louis, Mo.) in 50 µL of water. The reaction mixture was vortexed briefly, incubated at room temperature for another 5 minutes and subjected to following purification steps.

The reaction mixture was first purified through PD10 Sephadex G25M sizing column (Pharmacia, Piscataway, N.J.) preequilibrated and eluted with labelling buffer containing 0.1% BSA. The flow rate of the elution was maintained at 1 mL/min and 20×0.8 minute fractions were collected. The tracer which appeared in the void volume as the first RLU peak (fractions 6–9) was located by taking a 10 µL sample from each fraction, diluting it 200-fold with labelling buffer, and counting 10 µL of the diluted sample on a MLA II luminometer (Ciba Corning Diagnostics, Medfield, Mass.). The desired pooled fractions were concentrated with a centricon-30 to about 300 µL. The concentrate was subjected to further HPLC gel filtration.

Waters HPLC system (Waters Associate, Milford, Mass.) mounted with a Protein Pak 300SW HPLC gel filtration column (Waters #11787) was first equilibrated with HPLC column buffer containing 50 mM Tris pH 8, 0.25M MgCl$_2$, 0.1% BSA, and 0.01% Triton X-100. The labeled virus concentrate from the PD10 column was loaded onto the 300SW column. The elution was maintained at a flow rate of 0.5 mL/min and 40×0.25 mL fractions were collected beginning from 11 minute after sample injection. The labeled virus peak (retention times of 13–17 minutes) was again identified in the same manner as above, by looking for the first RLU peak through counting samples of the collected fractions. The fractions containing the first RLU peak were pooled and represented the purified labeled virus tracer.

B) Preparation of Anti-Human IgG Solid Phase

Mouse anti-human IgGFc monoclonal antibody was covalently linked to PMP with glutaraldehyde (in 20 mM sodium phosphate, pH 7). This is a modification of the method described in BioTechniques 3, 156 (1985).

C) Preparation of Monoclonal Anti-Human IgGFc (Clone 157.8D6.5D3)

Fusion Procedure: Method uses polyethylene glycol to fuse isolated mouse spleen cells from immunized donors with SP2/0 Ag4-1 mouse myeloma cells (Galfrie and Milstein, (1981), Methods in Enzymology 73:3).

Screening Procedure: Secretion of specific antibody was tested for by the ability of the cell supernatant to link acridinium ester labeled human IgG to human IgG immobilized on paramagnetic particles. The monoclonal antibody was shown to be specific for human IgGFc and nonreactive to human IgG Fab and $Fab_2$ fragments, human IgA, IgM, IgE, and IgD when tested by western blot (as per Proc. Nat. Acad. Sci. U.S.A., 76: 4350 (1979)).

Antibody Isotype: The antibody isotype is IgG1, identified by using the Zymed MonoAb ID EIA kit (Zymed Lab Inc., San Francisco, Calif.).

D) Preparation of Monoclonal Anti-Rubella Antibody (Clone ML109.10E7.4A3)

Fusion Procedure: same as above.

Screening procedure: Secretion of specific antibody was tested for by the ability of the cell supernatant to bind rubella virus. The monoclonal binding to antigen was detected by ELISA (as per J. E. Coligan, Current Protocols in Immunology Vol. 1 (1991) section 2.1.3). Clones were shown to be specific by nonreactivity to uninfected culture controls.

E) Rubella IgG Capture Chemiluminescence Immunoassay

Performance of the different rubella virus tracers was evaluated in a manual Magic Lite® (Ciba Corning Diagnostics, Medfield, Mass.) assay format in triplicate. All serum samples were diluted five-fold with the diluent (1×DPBS, BioWhittaker, Walkersville, Md.) containing 50% calf serum, 1% Triton X-100, 1% normal mouse serum, and 0.1% sodium azide. Diluted sample (50 μL), Anti-human IgG solid phase (80 μg in 250 μL), and diluted rubella virus tracer (100 μL) were incubated together for 7.5 minutes at 37° C. in a Sarstedt polystyrene tube (Newton, N.C.). The reaction mix was separated, aspirated and washed twice with 1 mL 1×DPBS (BioWhittaker, Walkersville, Md.). The final pellet was reconstituted with 100 μL of water and its chemiluminescence measured on MLA-II luminometer (Ciba Corning Diagnostics, Medfield, Mass.).

Since the two rubella virus tracers (prepared as described above) varied in their specific chemiluminescence activity, the titering study was conducted over different ranges of input counts, using nine rubella IgG samples as shown in Table 3.

TABLE 3

Rubella IgG Capture Assay Results of NSP-DMAE Rubella Titering Study

| | Sample NSP-DMAE Rubella (RLU, % CV, P/N) | | | | | |
|---|---|---|---|---|---|---|
| | $1 \times 10^6$ | $5.95 \times 10^6$ | $11.1 \times 10^6$ | $13.3 \times 10^6$ | $24.3 \times 10^6$ | $46.1 \times 10^6$ |
| Diluent | 1233 | 1793 | 2473 | 2757 | 4253 | 9360 |
| % CV | 1.9 | 2.6 | 9.4 | 3.3 | 5.5 | 17.2 |
| P/N | 1.0 | 0.9 | 1.0 | 0.8 | 1.1 | 1.6 |
| Negative | | | | | | |
| RAB 17 | 1233 | 2037 | 2447 | 3367 | 4023 | 5987 |
| % CV | 3.3 | 20.1 | 3.9 | 23 | 8.5 | 7.5 |
| P/N | 1.0 | 1.0 | 1.0 | 1.0 | 1.0 | 1.0 |
| RAB 36 | 1383 | 1897 | 2587 | 2880 | 6357 | 8357 |
| % CV | 13.3 | 13.2 | 4.7 | 0.9 | 16.3 | 21.7 |
| P/N | 1.1 | 0.9 | 1.1 | 0.9 | 1.6 | 1.4 |
| Low + | | | | | | |
| CAP 10 | 1393 | 2903 | 4247 | 5613 | 8100 | 14830 |
| % CV | 2.7 | 6.1 | 2.4 | 6.4 | 9.1 | 7.6 |
| P/N | 1.1 | 1.4 | 2.2 | 2.1 | 2.6 | 3.3 |
| CAP 15 | 1473 | 3170 | 5283 | 7003 | 10263 | 19737 |
| % CV | 2.7 | 3 | 3.2 | 2.7 | 6.3 | 7.9 |
| P/N | 1.2 | 1.6 | 2.2 | 2.1 | 2.6 | 3.3 |
| Mid-High + | | | | | | |
| TSI 3156 | 3547 | 14420 | 32143 | 40403 | 66857 | 142657 |
| % CV | 3.8 | 3.3 | 4 | 3.2 | 1.3 | 1 |
| P/N | 2.9 | 7.1 | 13.1 | 12.0 | 16.6 | 23.8 |
| RAB 67 | 10970 | 52003 | 120987 | 151000 | 262317 | 536050 |
| % CV | 2.7 | 6.4 | 5 | 2.4 | 1.06 | 2.3 |
| P/N | 8.9 | 25.5 | 49.4 | 44.8 | 65.2 | 89.5 |
| TSI 3167 | 7357 | 35337 | 75027 | 94530 | 167653 | 342447 |
| % CV | 1.9 | 1.9 | 8 | 3.4 | 4.6 | 3.5 |
| P/N | 6.0 | 17.3 | 30.7 | 28.1 | 41.7 | 57.2 |
| TSI 3163 | 11270 | 56443 | 111327 | 142290 | 249450 | 51440 |
| % CV | 2.2 | 3.3 | 4.9 | 1.7 | 2.2 | 10.6 |
| P/N | 9.1 | 27.7 | 45.5 | 42.3 | 62.0 | 85.9 |
| DL1-3150-388 | 11477 | 55093 | 113783 | 146473 | 263267 | 542483 |
| % CV | 1.4 | 6.5 | 12.3 | 3.2 | 3.2 | 3.4 |
| P/N | 9.3 | 27.0 | 46.5 | 43.5 | 65.4 | 90.6 |

The DMAE labeled rubella tracer was titered over a wider range due to a 4–5 fold greater degree of incorporation of DMAE into the labeled virus tracer compared to NSP-DMAE. In order to compare assay conditions using a comparable mass of rubella tracers, the DMAE rubella tracer total input range must be several times higher than that of NSP-DMAE rubella condition. The titering study results demonstrated improved P/N ratios as the level of NSP-DMAE rubella tracer increased, while the P/N ratios generated by DMAE rubella tracer plateaued at $10 \times 10^6$ RLU/test. The selection of $24 \times 10^6$ RLU/test as the optimal input level for the NSP-DMAE rubella tracer was based on the results of higher P/N ratios, while maintaining low nonspecific binding with the control diluent. The comparable assay conditions using DMAE rubella tracer is $125 \times 10^6$ RLU/test. When these two conditions are compared, it is clear that NSP-DMAE rubella tracer is the superior reagent with P/N ratios ranging from 2 to 4 fold greater than those generated by DMAE rubella tracer.

The testing of these two rubella tracers was expanded to a population of twenty rubella IgG samples (ranging from 0.3–500 IU/mL) and 4 potential crossreactive samples (all identified as rubella IgG negative by Rubazyme assay (Abbott Labs, Chicago, Ill.) (Table 4A).

Figure 6:
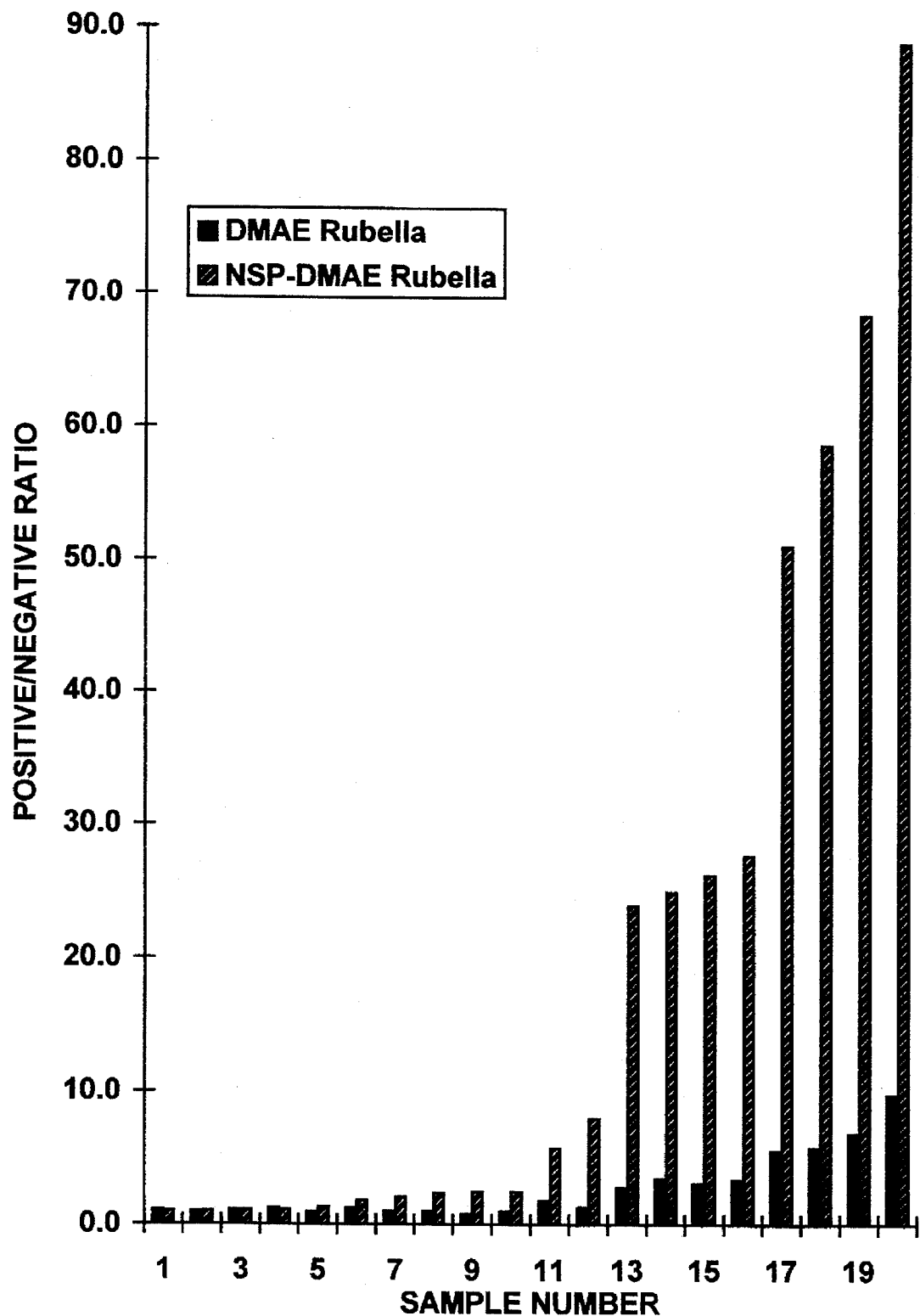
FIG. 6 is a bar graph showing a population study comparing the positive to negative ratio of assay results using the compounds of the instant invention as compared with DMAE rubella assay.

The study was conducted using the following total inputs for each reagent; NSP-DMAE rubella tracer ($24 \times 10^6$ RLU/test) and DMAE rubella tracer ($125 \times 10^6$ RLU/test). The population data suggested that the sensitivity of the rubella IgG capture assay is affected markly by the class of the PAAE utilized to directly label the virus. The P/N (positive to negative result) ratios generated from employing NSP-DMAE rubella tracer are considerably greater than those generated by the DMAE rubella tracer (FIG. 6). These results reflect the ability of the assay performed with hydrophilic NSP-DMAE rubella tracer to more clearly distinguish positive samples from negative samples than conventional DMAE tracer. This is particularly important in the diagnostically critical low positive population.

The impact of hydrophilic NSP-DMAE rubella tracer on the specificity of the potentially crossreactive samples was evaluated. Using a P/N ratio cutoff corresponding to the CAP10 sample, the results indicate no false positive identifications resulting from the use of the rubella tracers with these types of samples (Table 4B).

The results of both of these studies clearly suggest NSP-DMAE-NHS is a superior reagent for the direct labelling of rubella virus. This reagent results in a rubella preparation which specifically binds to a wide range of rubella IgG levels to produce specific RLU values which are clearly distinguishable from those of a rubella IgG negative population. Furthermore, these conditions exist without incurring false positive results with potentially crossreactive samples.

TABLE 4A

Population study using NSP-DMAE Rubella and DMAE Rubella Tracers

| | Rubella IgG Capture Assay (P/N ratio) | |
|---|---|---|
| Sample | NSP-DMAE Rubella | DMAE Rubella |
| RAB17 | 1.0 | 1.1 |
| APO5874-4 | 1.0 | 1.0 |
| ASO4912-9 | 1.1 | 1.1 |
| RAB 36 | 1.1 | 1.2 |
| AS14837-8 | 1.3 | 1.0 |
| CAP 10 | 1.8 | 1.2 |
| ASO1721-3 | 2.1 | 1.0 |
| AP27771-3 | 2.4 | 1.0 |
| AR99860-4 | 2.5 | 0.8 |
| CAP 15 | 2.5 | 1.0 |
| TSI 3164 | 5.8 | 1.8 |
| ASO6137-4 | 8.0 | 1.3 |
| GP1-27 | 23.9 | 2.8 |
| AP41719-0 | 24.9 | 3.5 |
| GP2-9 | 26.2 | 3.1 |
| GP2-18 | 27.7 | 3.4 |
| AR86731-7 | 51.1 | 5.6 |
| AR96863-2 | 58.7 | 5.9 |
| AS15758-2 | 68.5 | 6.9 |
| AR74744-4 | 88.9 | 9.8 |

TABLE 4B

| INTERFERENCE | RUBELLA IgG CAPTURE ASSAY | | RUBAZYME |
|---|---|---|---|
| SAMPLES (ALL RUBELLA IgG NEGATIVE) | NSP-DMAE RUBELLA P/N RATIO | DMAE RUBELLA P/N RATIO | > or = 1.0 is POSITIVE INDEX |
| EBV+ E9-3204-467 | 1.5 | 1.1 | 0.725 |
| EBV+ E8-2405-99 | 1.01 | 0.98 | 0.171 |
| VZV+ E02606-135 | 1.4 | 1.1 | 0.183 |
| ANA+ 12615M-910513 | 1.7 | 1.1 | 0.793 |

F) Comparison with Ciba Corning Magic Lite® Control Assay and Abbott IMx Assay

The evaluation of NSP-DMAE rubella tracer was extended even further, to include an investigation of how this Magic Lite® rubella IgG assay using NSP-DMAE rubella tracer compares with (1) Ciba Corning Diagnostics Magic Lite® assay (which uses a complex of unlabelled rubella and NSP-DMAE labeled anti-rubella monoclonal antibody 10E7) and (2) IMx Rubella IgG (Abbott, Chicago, Ill.). The sample population tested by both Magic Lite® assays included thirty-nine rubella IgG samples identified as positive or negative for rubella specific IgG by IMx (Table 5). It is interesting to note that the Positive result/Negative result (P/N) ratios generated by NSP-DMAE rubella tracer are significantly greater than observed with the Magic Lite® control assay format. This is particularly evident in the rubella IgG high positive samples and may reflect competition between the rubella specific IgG and the NSP-DMAE-MAb10E7 tracer for binding sites on the unlabelled rubella virus. Based on a P/N ratio cutoff corresponding to the CAP10 sample, the Magic Lite® rubella IgG assay utilizing NSP-DMAE rubella tracer demonstrated 97.4% agreement with the Magic Lite® rubella control assay and 92.3% agreement with IMx rubella IgG.

TABLE 5

Expanded population study using NSP-DMAE Rubella Tracer

| Sample | NSP-DMAE Rubella | Rubella + NSP-DMAE10E7 | IMx |
|---|---|---|---|
| RAB 17 | 1.0 | 1.0 | negative |
| AP05874-4 | 1.0 | 0.9 | negative |
| AS04912-9 | 1.1 | 0.9 | negative |
| RAB 36 | 1.1 | 1.0 | negative |
| AS14837-8 | 1.3 | 0.9 | negative |
| CAP 10 | 1.8 | 1.1 | positive |
| AS01721-3 | 2.1 | 1.05 | negative |
| AP27771-3 | 2.4 | 1.1 | negative |
| AR99860-4 | 2.5 | 1.1 | negative |
| CAP 15 | 2.5 | 1.2 | positive |
| AS00541-9 | 2.8 | 1.2 | positive |
| AR97400-3 | 3.2 | 1.3 | positive |
| AP41598-1 | 4.0 | 1.50 | positive |
| TSI 3164 | 5.8 | 2.0 | positive |
| AS06137-4 | 8.0 | 1.7 | positive |
| AS00407-3 | 9.9 | 2.4 | positive |
| TSI 3156 | 13.6 | 3.0 | positive |
| GP2-3 | 23.4 | 3.7 | positive |
| GP1-27 | 23.9 | 3.6 | positive |
| AP41719-0 | 24.9 | 2.6 | positive |
| GP2-9 | 26.2 | 3.9 | positive |
| GP1-1 | 26.3 | 3.7 | positive |
| GP2-11 | 26.9 | 4.1 | positive |
| GP2-18 | 27.7 | 4.1 | positive |
| GP2-4 | 28.1 | 4.4 | positive |
| TSI 3167 | 33.4 | 6.2 | positive |
| GP2-22 | 39.7 | 5.4 | positive |
| GP2-14 | 42.0 | 4.1 | positive |
| GP1-17 | 43.3 | 7.4 | positive |
| GP2-35 | 44.6 | 7.8 | positive |
| TSI 3163 | 48.7 | 13.1 | positive |
| AS15788-7 | 49.3 | 5.3 | positive |
| DL1-3510-388 | 51.0 | 11.6 | positive |
| AR86731-7 | 51.1 | 9.6 | positive |
| AR96863-2 | 58.7 | 10.6 | positive |
| AP35925-6 | 62.0 | 7.9 | positive |
| HG68085-5 | 63.8 | 16.5 | positive |
| AS15758-2 | 68.5 | 11.3 | positive |
| AR74744-4 | 88.9 | 27.9 | positive |

EXAMPLE 11

DMAE & NSP-DMAE Labeling of Protein

This example shows that a larger quantity of NSP-DMAE can be covalently attached to a protein, such as BSA (bovine serum albumin) because of the hydrophilic nature of NSP-DMAE.

A solution of BSA (10 mg, 150 nmol) in 0.1M carbonate buffer, pH 9, (2.7 mL) was treated with a solution of 50 equivalents of either DMAE-NHS ester or NSP-DMAE-NHS ester (4.5 mg each, 7.5 mmol) in DMF (300 mL). The reaction utilizing DMAE-NHS was slightly cloudy whereas the reaction with NSP-DMAE-NHS remained completely clear throughout the reaction. The reactions were stirred at room temperature for 24 hours and the labeled proteins were isolated by size-exclusion chromatography on a Sephadex G-25 column (3.7×42 cm) eluted with 10 mM phosphate buffer pH 8. The protein fraction was collected in each case, concentrated and repurified on the same Sephadex G-25 column. After the second concentration, the quantity of the labeled protein recovered from each reaction and the extent of Acridinium Ester (AE) labeling was estimated by performing a protein analysis (Bio-Rad protein assay) and by measuring the chemiluminescent activity of the labeled protein, respectively. From these measurements, the protein was found to be labeled with approximately 14 DMAE molecules and 24 NSP-DMAE molecules.

EXAMPLE 12

Conjugation of NSP-DMAE Labeled BSA (Bovine Serum Albumin) to 5'-32P-labeled 508.CF-3'-Maleimide This example shows how the protein carrier pre-labeled with plurality of NSP-DMAE can be covalently attached with a 24-mer oligonucleotide which we called 508.CF-NH2. The oligonucleotide was first radio-labeled with 32-P at the 5'-end phosphate using the conventional radio-labeling technique commonly known to those skilled in the arts. The purpose of 32P-labeling of the oligonucleotide was to provide a handle to quantify the oligonucleotide once conjugated with the protein carrier. The 3'-end of the oligonucleotide carries an aminoalkyl group to allow the reaction with a bi-functional cross-linker as described below so that a sulfhydryl-reactive maleimido group can be attached. Methods of preparing oligonucleodie with aminoalkyl group at the 3'-end is well known (See User's Manual on DNA Modification Reagents for Use in Automated DNA Synthresis, Doc. No. PB022789-1, CLONTECH Laboratories, Inc., Palo Alto, Calif., 1989).

Preparation of 32P-labeled 508.CF-maleimide

A solution of 32P-508.CF-NH2 (40 nmoles) in 50 mM carbonate (600 mL, pH 8.4) was treated with sulfosuccinimidyl 4-(N-maleimidomethyl)cyclohexane-1-carboxylate (sulfo-SMCC, 10 mg, 22.9 mmol). The reaction was stirred at room temperature for 30 minutes following which the product was purified directly by preparative HPLC on a C8 column (0.7×25 cm) using a gradient of 8% to 20% acetonitrile in 0.1M triethylammonium acetate buffer, pH 7.0, over 20 minutes at a flow of 2.3 mL/min and UV detection at 260 nm (tR=14.8 min. product; tR=12.7 min. starting material). The eluent off the "HPLC" containing the product was lyophilized to dryness: yield 25 nmoles (60%).

Conjugation of the NSP-DMAE Labeled BSA to 32P-508.CF-maleimide (NSP-DMAE)21-BSA was prepared by reacting BSA with 30 equivalents of NSP-DMAE-NHS as described above. The labeled protein (6 mg, 90 nmole) in 100 mM phosphate buffer containing 5 mM EDTA, pH 8, was treated with 2-iminothiolane (50 equivalents, o.6 mg, Pierce, Rockford, Ill.).

The reaction was stirred under nitrogen at room temperature for 1 hour. The thiolated protein was then isolated by size-exclusion chromatography on a column of Sephadex G-25 (3.7×42 cm) using 20 mM phosphate, 1 mM EDTA, pH 6.8, as eluent. The protein fraction off the column was concentrated to a volume of approximately 2 mL in a speed-vac. The protein solution was then mixed with 5'-32P-labeled 508.CF-3'-maleimide (8.9 nmole) and the resulting solution was stirred at room temperature under nitrogen for 16 hours. The reaction was then quenched by the addition of 600 nmole of bromoacetic acid.

After stirring for an additional 2 hours at room temperature, the reaction mixture was concentrated to a volume of about 0.5 mL by centrifugal ultrafiltration. A mixture of the conjugate and unconjugated protein was separated from unreacted 508.CF-maleimide by native Polyacrylamide Gel Electrophoresis (PAGE) on a 7.5% density gel (3% cross-linked) in TBE buffer, pH 8, run at constant current of 10 mA at 4 deg C. The mixture of the conjugate and the unconjugated protein was eluted from the gel matrix by a crush and soak method in PBS buffer (138 mM NaCl, 8.1 mM Na2HPO4, 2.7 mM KCl, 1.2 mM KH2PO4, pH 7.4).

To further separate the conjugate which incorporates the oligonucleotide, from the unconjugated protein, an affinity purification is called for. A typical example of separating the conjugate with the incorporated oligonucleotide from the contaminating unconjugated protein is the utilization of a solid phase (e.g. functionalized polystyrene or controlled pore glass) immobilized with the complementary oligonucleotide. By performing a hybridization, separation, and washing steps, one can capture the desired conjugate onto the solid phas, wash away the unconjugated protein, and continue on with a releasing step to regain the purifed conjugate from the solid phase. Such purification/enrichment steps can be easily done by those skilled in the arts of nucleic acid hybridization.

EXAMPLE 13

Preparation of Antibody-DNA (anti-TSH-508.CF) Conjugate

This example further illustrates the range of uses for the compounds of the instant invention. In this example antibody-DNA conjugate suitable for carrying a large number of chemiluminescent tags is generated. The conjugate can be prepared in three steps using an alternative thiol-maleimido coupling chemistry.

Preparation of Thiolated anti-TSH and Conjugation to Maleimide-508.CF

A solution of anti-TSH (20 mg, 133 nmoles) in 2 mL 0.2M phosphate buffer, pH 8, containing 150 mM NaCl and 5 mM EDTA was treated with 2-iminothiolane (Traut's reagent, 0.37 mg, 20 equivalents) under nitrogen. The reaction was stirred at room temperature for 1 hour under nitrogen and the thiolated protein was isolated by size-exclusion chromatography on a column of Sephadex G-25 (3.7×42 cm) using 10 mM phosphate, pH 6.8, containing 0.5 mM EDTA as eluent. The protein fraction eluting off the column (yield 17 mg, 113 nmoles) was concentrated under reduced pressure in a speed-vac to a volume of approximately 2 mL. This solution was then mixed with maleimide-508.CF (12 nmoles). The reaction was stirred at room temperature for 24 hours under nitrogen by which time the solution had turned slightly cloudy.

The reaction mixture was then loaded on a column of DEAE-cellulose (1×15 cm) equilibrated with 20 mM phosphate, pH 7. The column was eluted with a gradient of 0 to 200 mM NaCl in 20 mM phosphate, pH 7, followed by 200 mM NaCl in 20 mM phosphate, pH 7, to elute excess unreacted protein. Elution with 500 mM NaCl in the same buffer, eluted a mixture of the conjugate and unreacted DNA. Following concentration of the high salt fraction off the ion-exchange column by ultrafiltration, separation of the conjugate from unreacted DNA was achieved by size-exclusion chromatography on a column of Sephadex G-75 (1.5×40 cm) using water as eluent at 0.5 mL/min. The solution of the conjugate isolated by this procedure was lyophilized to dryness.

Characterization of the conjugate and calculation of conjugate yield was performed by UV spectrophotometry. The UV spectrum of the conjugate isolated by the procedure described above was identical in appearance to that of a 1:1 mixture of 508.CF and anti-TSH. This UV spectrum was characterized by an absorption maximum at ~270 nm and a 1:1 correspondence between the $A_{260}$ and $A_{280}$ values. The value of $A_{260}$ and $A_{280}$ in the UV spectrum of the conjugate was increased by a factor of 1.5 when compared with DNA alone and protein alone respectively. From this result, the yield of the 1:1 conjugate of 508.CF and anti-TSH was calculated to be 1.6 nmoles (13% overall from maleimide 508.CF).

The conjugates thus produced can be covalently linked to NHS-DMAE chemiluminescent label by the previously described procedures, among others.

What is claimed is:

1. An acridinium ester of the following formula:

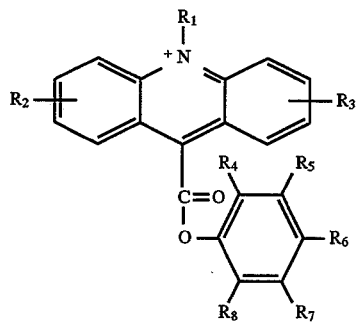

wherein $R_1$ is alkyl, alkenyl, alkynyl, aryl, or aralkyl, having up to 24 carbons and 1 to 20 heteroatoms selected from the group consisting of nitrogen, oxygen, phosphorous and sulfur; and $R_2, R_3, R_5,$ and $R_7$ are hydrogen, amino, hydroxyl, halide, nitro, —CN, —SO$_3$H, —SCN, -R, —OR, —NHCOR, —COR, —COOR, or —CONHR, wherein R is alkyl, alkenyl, alkynyl, aryl, or aralkyl, having up to 24 carbons and up to 20 heteroatoms selected from the group consisting of nitrogen, oxygen, phosphorous, and sulfur; and $R_4$ and $R_8$ are alkyl, alkenyl, alkynyl, aralkyl, or alkoxyl having up to 8 carbons, with no branching wherein the side chain groups have more than 2 carbons; and $R_6$ represents the following substitutions: $R_6=R_9-R_{10}$ wherein $R_9$ is not required but optionally can be an alkyl, or aralkyl group having up to 5 heteroatoms which can be P, S, N, or O, and $R_{10}$ is an electrophile, a leaving group, a group with these two combined natures, or selected from the following structures;

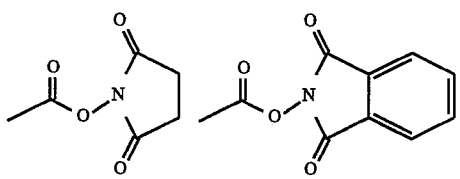

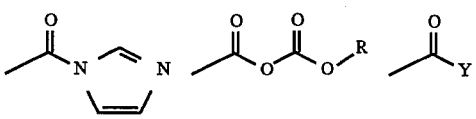

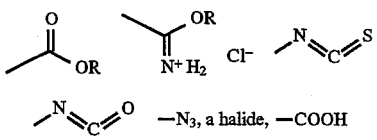

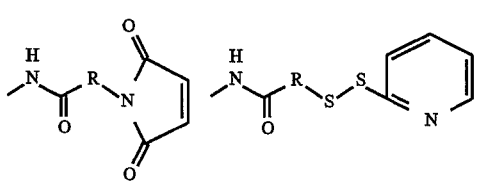

where Y is a halide and R is an alkyl, aryl, or aralkyl group; and where $R_5$, $R_6$, and $R_7$ substituent positions on the phenoxy ring are interchangeable.

2. An acridinium ester of claim 1 where $R_1$ is a sulfopropyl or sulfoethyl group; $R_2$ is a hydrogen, methoxy, ethoxy, nitro, or halogen; $R_3$, $R_5$, and $R_7$ are hydrogen; $R_4$ and $R_8$ are methyl, ethyl, or isopropyl groups; and $R_6$ is N-succinimidyloxycarbonyl, N-succinimidyloxycarbonylalkyl, or carboxylate.

3. An acridinium ester of claim 1 conjugated to a compound or macromolecule, said conjugation being either by direct covalent bonding between the acridinium ester and the compound or macromolecule or by indirect covalent bonding through a spacer.

4. An acridinium ester of claim 3 where the conjugation is through a spacer and the spacer is provided by a bifunctional cross-linker.

5. An acridinium ester of claim 4 where the the bifunctional cross-linker is hexyl-1,6-diamine, ethylene diamine, or aminocaproic acid.

6. An acridinium ester of claim 3 where the macromolecule is selected from the group consisting of protein, peptide, inactivated protein, DNA, RNA, oligonucleotide, neurotransmitter, hormone, steroid hormone, virus, bacterium, toxin and cytokine.

7. An acridinium ester of claim 6 where the protein is selected from the group consisting of antibody, antibody fragments, avidin, streptavidin, allergen, receptor protein, DNA binding protein, viral antigen, and bacterial antigen.

8. An acridinium ester of claim 3 where the compound is a hapten or small biologically active molecule.

9. An acridinium ester of claim 8 where the hapten is a steroid hormone.

10. An acridinium ester of claim 9 where the steroid hormone is testosterone, the conjugation is by indirect covalent bonding through a spacer, and the spacer and the testosterone are connected by a C19-C linkage, an olefinic C19 linkage, or a C19-O linkage.

11. An acridinium ester of claim 9 where the steroid hormone is testosterone, and where the conjugation is through a spacer and the spacer is provided by a bifunctional cross-linker selected from the group consisting of hexyl-1, 6-diamine, ethylene diamine, and aminocaproic acid.

12. An acridinium ester of claim 9 where said steroid hormone is a testosterone derivative selected from the group consisting of:

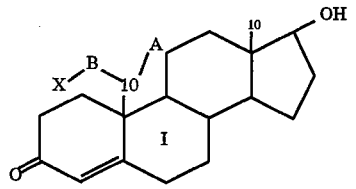

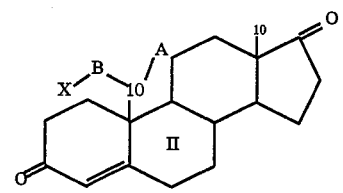

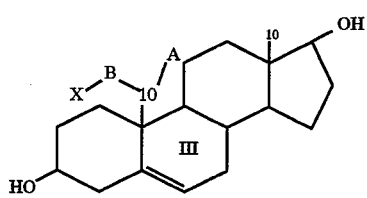

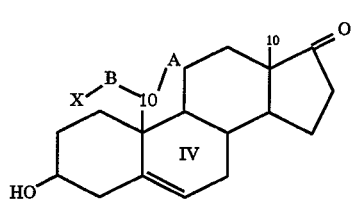

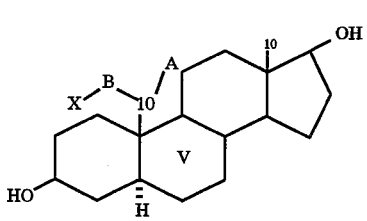

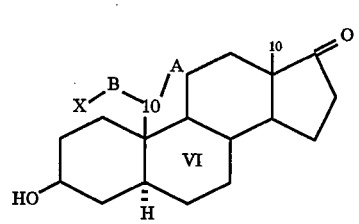

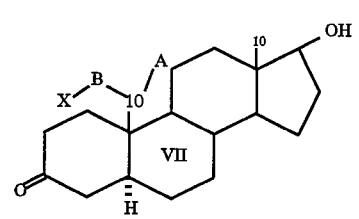

13. An acridinium ester of claim 3 where the macromolecule is Rubella virus.

14. A method of synthesis of an acridine ester comprising the step of combining a compound of the formula:

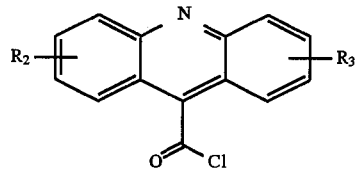

with a compound of the formula

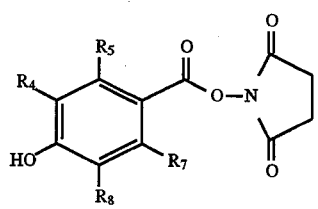

to form an acridine ester, where $R_2$, $R_3$, $R_5$, and and $R_7$ are hydrogen, halide, nitro, -R, —OR, —CN, —NHCOR, —COR, —COOR, or —CONHR, where R is alkyl, alkenyl, alkynyl, or aralkyl, and where $R_4$ and $R_8$ are alkyl, alkenyl, alkynyl, aralkyl, or alkoxyl having up to 8 carbons, with no branching wherein the side chain groups have more than 2 carbons.

15. A method of synthesis of DMAeE-NHS comprising combining a compound of the formula:

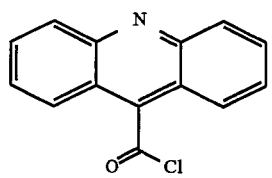

with a compound of the formula:

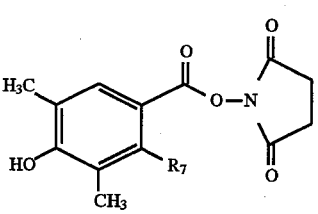

to form DMAeE-NHS.

16. An acridinium ester conjugate comprising an oligonucleotide conjugated to a macromolecule, said macromolecule being conjugated to multiple acridinium esters of claim 1.

17. An acridinium ester conjugate of claim 1, wherein said oligonucleotide is a gene probe.

18. An acridinium ester conjugate of claim 16 wherein in addition to being conjugated to multiple acridinium esters of claim 1, said macromolecule is also conjugated to multiple hydrophilic polymers.

19. An acridinium ester conjugate of claim 18 wherein the hydrophilic polymer is polyethylene glycol.

20. An acridinium ester conjugate comprising an oligonucleotide conjugated to a macromolecule, said macromolecule being conjugated to (a) multiple hydrophilic polymers and (b) multiple acridinium esters having the following formula:

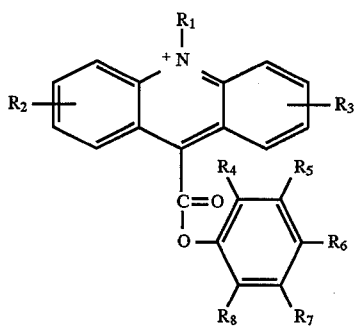

wherein

R₁ is alkyl, alkenyl, alkynyl, aryl, or aralkyl, having up to 24 carbons and up to 20 heteroatoms selected from the group consisting of nitrogen, oxygen, phosphorous and sulfur; and R₂, R₃, R₅, and R₇ are hydrogen, amino, hydroxyl, halide, nitro, —CN, —SO₃H, —SCN, -R, —OR, —NHCOR, —COR, —COOR, or —CONHR, wherein R is alkyl, alkenyl, alkynyl, aryl, or aralkyl, having up to 24 carbons and up to 20 heteroatoms selected from the group consisting of nitrogen, oxygen, phosphorous, and sulfur; and R₄ and R₈ are alkyl, alkenyl, alkynyl, aralkyl, or alkoxyl having up to 8 carbons, with no branching wherein the side chain groups have more than 2 carbons; and R₆ represents the following substitutions: R₆=R₉-R₁₀ where R₉ is not required but optionally can be an alkyl, or aralkyl group having up to 5 heteroatoms which can be P, S, N, or O, and R₁₀ is an electrophile, a leaving group, a group with these two combined natures, or selected from the following structures;

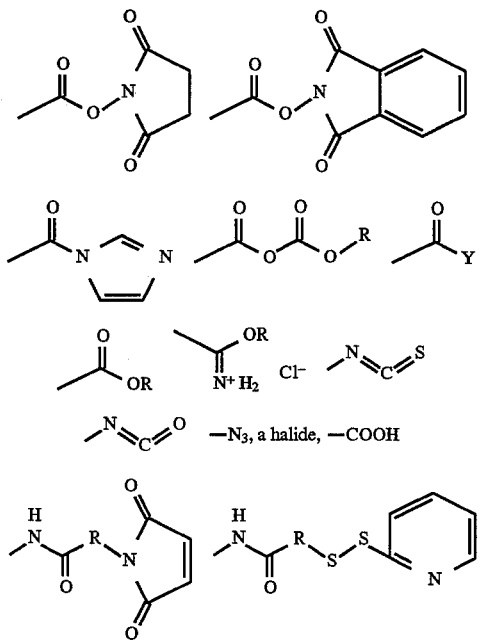

where Y is a halide and R is an alkyl, aryl, or aralkyl group; and where R₅, R₆, and R₇ sustituent positions on the phenoxy ring are interchangeable.

21. An acridinium ester conjugate of claim 20, wherein said oligonucleotide is a gene probe.

22. An acridinium ester conjugate of claim 20, wherein the hydrophilic polymer is polyethylene glycol.

23. A method of measuring the amount of an analyte in a biological fluid comprising performing an assay for the analyte on a sample of the biological fluid, said assay employing the acridinium ester of claim 1 as a label and comprising the steps of:

(A) causing the label to emit a light signal;
(B) detecting the light signal of step (A); and
(C) determining the amount of the analyte in the sample from the detected light signal of step (B).

24. The method of claim 23 wherein:

(1) the assay employs a detector molecule, which may optionally be a complex of two or more molecular entities;
(2) the detector molecule is labeled with the acridinium ester of claim 1;
(3) prior to step (A), the assay comprises the steps of:
 (i) contacting the sample with the detector molecule;
 (ii) sequestering bound detector and analyte; and
 (iii) washing away excess detector;
(4) steps (A) and (B) are performed on the sequestered and washed bound detector and analyte; and
(5) in step (C), the amount of the analyte in the sample is proportional to the detected light signal of step (B).

25. The method of claim 23 wherein:

(1) the assay employs a competitive tracer;
(2) the competitive tracer is labeled with the acridinium ester of claim 1;
(3) prior to step (A), the assay comprises the steps of:
 (i) contacting the sample with the competitive tracer and a specific binder for the analyte; and
 (ii) retrieving the specific binder;
(4) steps (A) and (B) are performed on the retrieved specific binder; and
(5) in step (C), the amount of the analyte in the sample is inversely proportional to the detected light signal of step (B).

26. The method of claim 23 wherein:

(1) the assay employs a competitive tracer;
(2) the competitive tracer is labeled with the acridinium ester of claim 1;
(3) prior to step (A), the assay comprises the steps of:
 (i) contacting the sample with the competitive tracer and a specific binder for the analyte; and
 (ii) retrieving the specific binder;
(4) steps (A) and (B) are performed on unbound competitive tracer; and
(5) in step (C), the amount of analyte in the sample is proportional to the detected light signal of step (B).

27. The method of claim 23 wherein:

(1) the assay employs a first specific binder and a second specific binder;
(2) the second specific binder is labeled with the acridinium ester of claim 1;
(3) prior to step (A), the assay comprises forming a sandwich of the first specific binder, the analyte, and the second specific binder by contacting the sample with the first and second specific binders;
(4) steps (A) and (B) are performed on the sandwich; and
(5) in step (C), the amount of analyte in the sample is proportional to the detected light signal of step (B).

28. The method of claim 23 wherein:
(1) the assay employs a detector and a competitive binder to the detector;
(2) the detector is labeled with the acridinium ester of claim 1;
(3) prior to step (A), the assay comprises the steps of:
  (i) contacting the sample with the labeled detector and a competitive binder to the detector;
  (ii) sequestering the labeled detector bound to the competitive binder; and
  (iii) washing away (a) excess detector and (b) detector bound to the analyte;
(4) steps (A) and (B) are performed on labeled detector bound to the competitive binder; and
(5) in step (C), the amount of analyte in the sample is inversely proportional to the detected light signal of step (B).

29. The method of claim 28 where a releasing agent is used.

30. The method of claim 28 where no releasing agent is used.

31. A method of detecting an analyte in a biological fluid comprising performing an assay for the analyte on a sample of the biological fluid, said assay employing the acridinium ester of claim 1 as a label, said assay comprising the steps of:

(A) causing the label to emit a light signal;

(B) detecting the light signal of step (A); and (C) determining the presence or absence of the analyte in the sample from the detected light signal of step (B).

* * * * *